United States Patent
Farren et al.

(10) Patent No.: US 12,023,424 B1
(45) Date of Patent: Jul. 2, 2024

(54) CONTINUOUS DISINFECTION OF HUMAN OCCUPIED SPACE

(71) Applicant: Myna Life Technologies, Inc., Oakland, CA (US)

(72) Inventors: Alexander Raymond Richard Farren, Oakland, CA (US); Noah Bareket, Saratoga, CA (US)

(73) Assignee: Myna Life Technologies, Inc., Oakland, CA (US)

(*) Notice: Subject to any disclaimer, the term of this patent is extended or adjusted under 35 U.S.C. 154(b) by 0 days.

(21) Appl. No.: 18/205,812

(22) Filed: Jun. 5, 2023

Related U.S. Application Data

(60) Provisional application No. 63/433,258, filed on Dec. 16, 2022.

(51) Int. Cl.
*A61L 9/20* (2006.01)

(52) U.S. Cl.
CPC ............ *A61L 9/20* (2013.01); *A61L 2202/25* (2013.01); *A61L 2209/111* (2013.01)

(58) Field of Classification Search
CPC ... A61L 9/20; A61L 2202/25; A61L 2209/111
See application file for complete search history.

(56) References Cited

U.S. PATENT DOCUMENTS

| | | | |
|---|---|---|---|
| 8,913,118 B2 | 12/2014 | Millikan | |
| 9,404,862 B2 | 8/2016 | Ehring | |
| 9,566,357 B2 | 2/2017 | Liao | |
| 10,088,358 B1* | 10/2018 | O'Driscoll | G01J 1/0219 |
| 10,485,887 B2 | 11/2019 | Ramanand | |
| 10,639,387 B2 | 5/2020 | Bonutti | |
| 2016/0175610 A1* | 6/2016 | Livingston | G01J 1/429 607/94 |
| 2017/0069192 A1 | 3/2017 | Sood | |
| 2017/0246329 A1* | 8/2017 | Lloyd | A61L 2/24 |
| 2017/0246331 A1* | 8/2017 | Lloyd | A61Q 17/04 |
| 2020/0179544 A1* | 6/2020 | Ufkes | H05B 47/125 |
| 2021/0346543 A1* | 11/2021 | Brooks | G02B 5/26 |
| 2022/0001062 A1* | 1/2022 | Le | A61L 9/20 |
| 2022/0059338 A1* | 2/2022 | Baxter | H01J 61/025 |
| 2022/0062463 A1* | 3/2022 | Ramer | H05B 47/16 |
| 2022/0062468 A1* | 3/2022 | Rodriguez | A61L 2/24 |
| 2022/0062475 A1* | 3/2022 | Johnson | B60Q 1/2611 |
| 2022/0072184 A1* | 3/2022 | Groves | A61L 2/08 |
| 2022/0105220 A1* | 4/2022 | Ufkes | A61L 2/26 |
| 2022/0111086 A1* | 4/2022 | Childress | A61L 9/20 |
| 2022/0193283 A1* | 6/2022 | Meskimen | B60Q 3/43 |
| 2022/0296764 A1* | 9/2022 | Roe | A61L 2/24 |

(Continued)

OTHER PUBLICATIONS

Author Unknown, COVID-19 Was Third Leading Cause of Death in U.S., CDC Newsroom, Apr. 22, 2022.

(Continued)

*Primary Examiner* — Regina M Yoo
(74) *Attorney, Agent, or Firm* — Van Pelt, Yi & James LLP

(57) ABSTRACT

Ultraviolet light is outputted in a space by one or more ultraviolet light sources. The presence of one or more people in the space is detected by one or more sensors. An ultraviolet light level delivered in the space while the space is occupied with one or more people is calculated based on a first output of the one or more ultraviolet light sources and a second output of the one or more sensors.

15 Claims, 21 Drawing Sheets

(56) References Cited

U.S. PATENT DOCUMENTS

2022/0347329 A1* 11/2022 Ramer .................. A61L 2/24
2022/0387638 A1* 12/2022 Ufkes .................. A61L 2/24
2023/0248862 A1*  8/2023 Benner ................. A61L 2/10
                                                         422/24

OTHER PUBLICATIONS

Carling et al., Identifying Opportunities to Enhance Environmental Cleaning in 23 Acute Care Hospitals, Infection Control & Hospital Epidemiology, Jan. 2008, vol. 29, Issue 1.
Eadie et al., Far-UVC (222 nm) Efficiently Inactivates an Airborne Pathogen in a Room-Sized Chamber, Scientific Reports, 2022.
Hayden et al., Risk of Hand or Glove Contamination after Contact with Patients Colonized with Vancomycin-Resistant Enterococcus or the Colonized Patients' Environment, Infection Control & Hospital Epidemiology, Feb. 2008, vol. 29, Issue 2.
Jefferson et al., A Novel Technique for Identifying Opportunities to Improve Environmental Hygiene in the Operating Room, AORN Journal, 2011.
Lei et al., Exploring Surface Cleaning Strategies in Hospital to Prevent Contact Transmission of Methicillin-Resistant *Staphylococcus aureus*, BMC Infectious Diseases, 2017.
Liu et al., A Rapid Coordinate Transformation Method Applied in Industrial Robot Calibration Based on Characteristic Line Coincidence, Sensors, 2016.
Memarzadeh et al., Role of Air Changes per Hour (ACH) in Possible Transmission of Airborne Infections, Building Simulation, 2012, pp. 15-28, vol. 5, No. 1.

* cited by examiner

MRSA concentrations dynamics in baseline scenario in 48-h simulation. (a) in MRSA-infected patient's room and HCW's hands, and (b) in susceptible patient's room. Note difference in scales on y-axis

| Domain | Species | Dose for 3 log reduction (mJ/cm²) | |
|---|---|---|---|
| | | 222 nm | 254 nm |
| Bacteria | MRSA (Methicillin-Resistant Staphylococcus aureus) | 15 | 10 |
| Bacteria | Pseudomonas aeruginosa Pseudomonas aeruginosa | 8 | 4 |
| Bacteria | Escherichia. coli O-157 | 9 | 5 |
| Bacteria | Salmonella Typhimurium | 10 | 4 |
| Bacteria | Campylobacter jejuni | 4 | 4 |
| Bacteria | Bacillus subtilis  Vegetative cell | 7 | 8 |
| Bacteria | Bacillus cereus  Spore | 44 | 90 |
| Bacteria | Clostridium difficile  Spore  JCMI1296 | 30 | 60 |
| Bacteria | Spore  JIR8094 | 32* | >86* |
| Virus | MS2  23 | 50 | |
| Virus | Feline calicivirus  24 | 24 | |
| Virus | Influenza A  H1N1, pdm09 strain A/Michigan/45/2015 | <6 | <6 |
| Virus | H1N1, A/PR/8/34  ATCC VR-1469 | 3 ** | - |
| Virus | H1N1, A/PR/8/34 | 2 *** | - |
| Virus | Alphacoronavirus Feline enteric coronavirus  WSU 79-1683 | 2 ** | - |
| Virus | Human coronavirus  229E VR-740 | 1.7 **** | - |
| Virus | Betacoronavirus  Human coronavirus  OC43 VR-1558 | 1.3 **** | - |
| Virus | SARS-CoV-2  2019-nCov/Japan/AI/I-004/2020 | 3.2 ***** | - |

Prior Art
FIG. 3

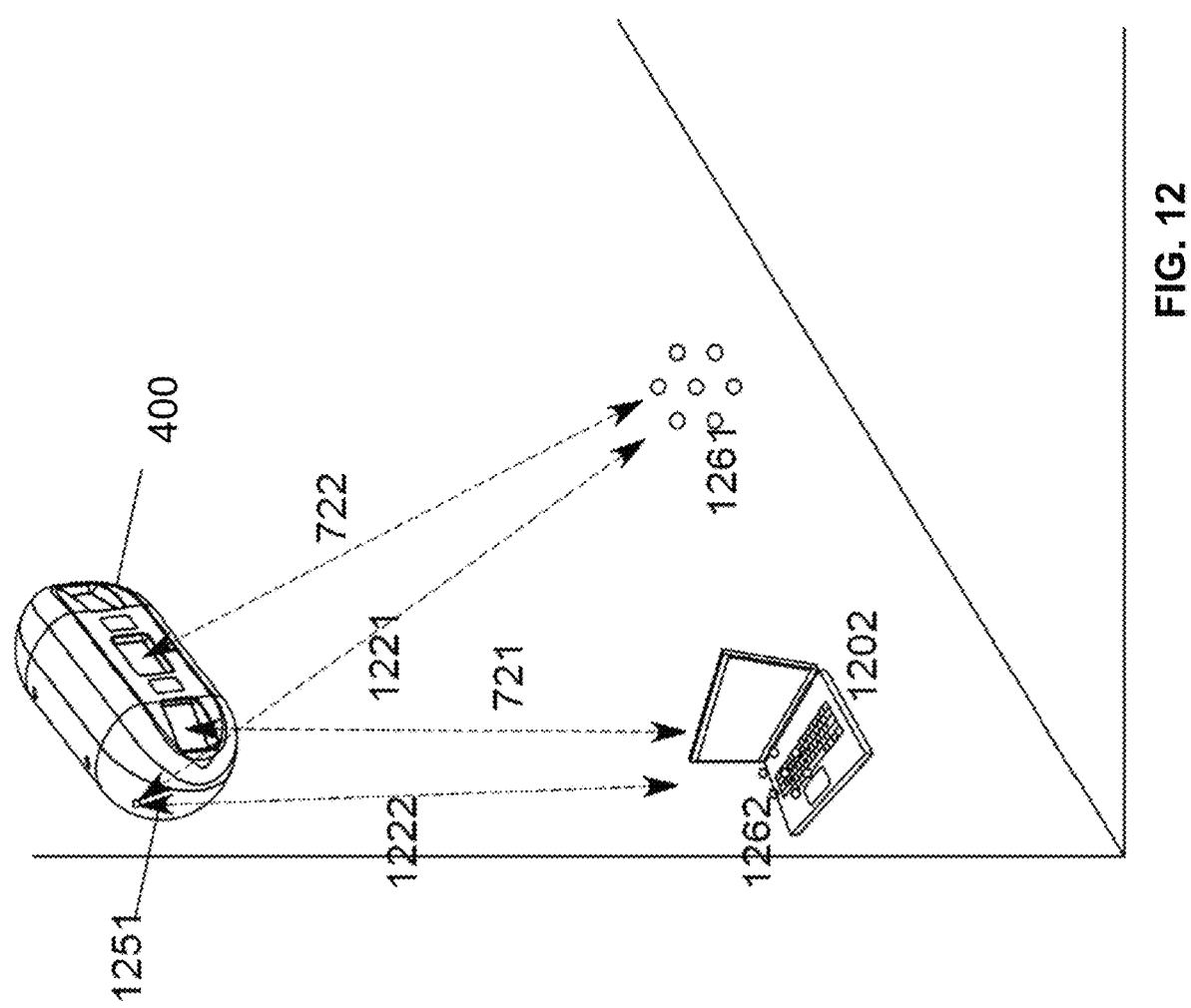

CONTINUOUS DISINFECTION OF HUMAN OCCUPIED SPACE

CROSS REFERENCE TO OTHER APPLICATIONS

This application claims priority to U.S. Provisional Patent Application No. 63/433,258 entitled CONTINUOUS DISINFECTION OF HUMAN OCCUPIED SPACE filed Dec. 16, 2022 which is incorporated herein by reference for all purposes.

BACKGROUND OF THE INVENTION

For many years, the need to disinfect rooms and other enclosures have been quite important. One example is hospital rooms.

Today, a common approach is for human cleaners to use chemical disinfectants. This approach is expensive for many reasons. First, the chemical disinfectants run out and must be replaced. This is a recurring expense that can be significant.

Second, these disinfectants are applied by human labor. Human labor is not only expensive, but also error-prone. Jefferson et al. found that about 50% of high-touch surfaces in the operating room are missed by crews using chemical disinfection: "For instance, in a 2008 study of 23 American hospitals, over 50% of surfaces in patient rooms were missed completely after patients were discharged. Cleaning rates fell below 30% for toilet handles, bedpan cleaners, light switches, and door knobs. . . . A Chicago study found VRE bacteria were transferred to gloved hands nearly half of the time after contact with bed rails, and 46% of handprint cultures grew VRE after just 5 seconds of contact with the bed rail."

This human error puts healthcare workers (HCW) and neighboring patients at risk of infection (which further compounds potential costs to the hospital). FIG. 1 depicts some of the ways pathogens can propagate through a hospital via the noses and hands of patients and health care workers, as well as via low and high touch surfaces.

Evidence for the effectiveness of higher frequency disinfections has already been examined and demonstrated. A 2017 study by Lei et al. modeled the methicillin-resistant *Staphylococcus aureus* (MRSA) concentration on surfaces in an intensive care unit (ICU) room where two disinfecting approaches were used. The study highlighted the greater effectiveness of manually wiping high touch three times an hour by healthcare workers as opposed to cleaning the entire room before patient activities. This study also indicates the utility of simple wipe disinfection on high touch surfaces even when they appear to be visibly clean and free of organic material. FIG. 2 depicts an image of two charts from the Lei study showing the effect of wiping visibly clean surfaces.

Although there was greater value to wiping high touch surfaces than low touch surfaces, doing both further decreased the spread of MRSA to neighboring rooms. Priority should always be given to high touch surfaces. Labor shortages as well as healthcare workers already being overburdened make a non-manual solution ideal.

The Lei model demonstrates that increasing the frequency even further to 18 wipe disinfections per hour further reduced MRSA contamination. This is highly impractical in a real world scenario.

Recently, a more efficient method of disinfecting enclosures has emerged: UV light devices. UV light destroys viruses and bacteria and renders them non-viable. FIG. 3 is a table showing the effect of UV light on pathogens. This approach improves upon the first method given that the UV lights must be replaced rarely compared with chemical disinfectants. Moreover, the UV light systems work automatically, without the need for human labor, and are less prone to error.

In 2021, the CDC indicated that SARS-CoV-2 was the third leading cause of death for the second consecutive year after heart disease and cancer. This underscored the importance of aerosols as a route of pathogen spread. This applies not only to SARS-CoV-2 but also to other pathogens such as influenza, measles, other human coronaviruses (SARS-CoV, Middle East Respiratory Syndrome MERS-CoV) and Respiratory Syncytial Virus (RSV) as well as bacteria and fungi.

Although masks and other PPI can reduce risk, high levels of compliance are required to be effective. As such, technologies that can address aerosol transmission routes are needed. Increasing air filtration either through auxiliary HEPA filtration units or by increasing the number of air exchanges only partially addresses aerosol transmission.

Typical air-changes-per-hour (ACH) are EACH-12ACH in various healthcare settings. In 2022, Eadie et al. demonstrated that 128-322 equivalent air-changes-per-hour could be achieved in a room with FarUV light sources. Thus, using this technology, pathogens can be removed in a matter of minutes as opposed to hours.

Direct UV exposure in a room is also a more immediate method of preventing pathogen transmission. In 2012, Memarzadeh et al. suggested that the most important factor in aerosol transmission is the path between the source of infection and the room exhaust. Placing the patient as near as possible to the exhaust had the greatest effect on reducing possible infection. This is not always practical because in general, room ventilation is designed to provide uniform airflow and even thermal distribution throughout a space. Thus, there is an inherent amount of air mixing that occurs, potentially distributing pathogenic particles throughout the space. Filtration of pathogens is also more time consuming and indirect: the pathogens must flow through to the filter where they are removed.

Although UV addresses both surfaces and aerosols simultaneously, it cannot be readily used in occupied spaces due to safety considerations and maximum allowable amount of UV light set by the American Conference of Governmental Industrial Hygienists (ACGIH) and the International Commission on Non-Ionizing Radiation Protection (ICNIRP). Different wavelengths have different threshold limit values (TLVs).

TLVs suggest that UV light disinfection systems should not operate with people present in the room being disinfected. Systems that use light sources with wavelengths between 254-295 nm are limited to only $6 mj/cm^\wedge 2$ and less whereas systems that use light sources with wavelengths under 222 nm can use a TLV of approximately $161 mj/cm^\wedge 2$ on eyes and $479 mj/cm^\wedge 2$ on skin or greater. A dose of $15 mj/cm^\wedge 2$ of 222 nm light is needed to achieve a 99.9% reduction of MRSA demonstrating the utility and practicality of these TLVs.

"Irradiance" is the instantaneous level of UV light, measured in power per unit area (for example, $W/m^\wedge 2$ or $mW/cm^\wedge 2$). "Dose" is cumulative energy per unit area (typically measured in $j/M^\wedge 2$, or $mj/cm^\wedge 2$, etc.). It is not an instantaneous measurement; but rather one that is integrated or cumulative over time.

Accordingly, both disinfecting methods—human-applied chemical disinfectants and UV light systems—share one major problem: the room must be empty of people during disinfecting. This is a problem because while people are in the room, pathogens take the opportunity to grow their numbers. So with these methods, there is a never-ending cycle of pathogen disinfecting, followed by pathogen growth, followed by pathogen disinfecting, and so on.

This problem of keeping people out of hospital rooms became acute in the wake of the SARS-CoV-2 pandemic that began in 2020. One reason for this was many hospitals kept patients for other diseases (e.g., cancer) out of their rooms in fear that SARS-CoV-2 virus was circulating in those rooms. This effort to keep such needy patients out of the hospital rooms resulted in many unfortunate health crises beyond SARS-CoV-2.

What is needed more than ever is a cost-effective, automatic system for disinfecting rooms and other enclosures continuously, when people are present in those enclosures, not just when they are absent.

BRIEF DESCRIPTION OF THE DRAWINGS

Various embodiments of the invention are disclosed in the following detailed description and the accompanying drawings.

FIG. 3 is a table showing the effect of UV light on pathogens.

FIG. 12 is a diagram illustrating a device with a sensor that can detect pathogens and adjust the UV transmission accordingly in accordance with some embodiments.

SUMMARY OF THE INVENTION

Systems and techniques to disinfect a room or space using UV light while monitoring presence and location of humans and using algorithm(s) that modulate the light sources so that a TLV is not reached for any person in the space is disclosed. The TLV may be a safety limit or other type of limit. The TLV may be compared to a UV Level, such as a dose, an irradiance level, or any other light level.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Figure 1:
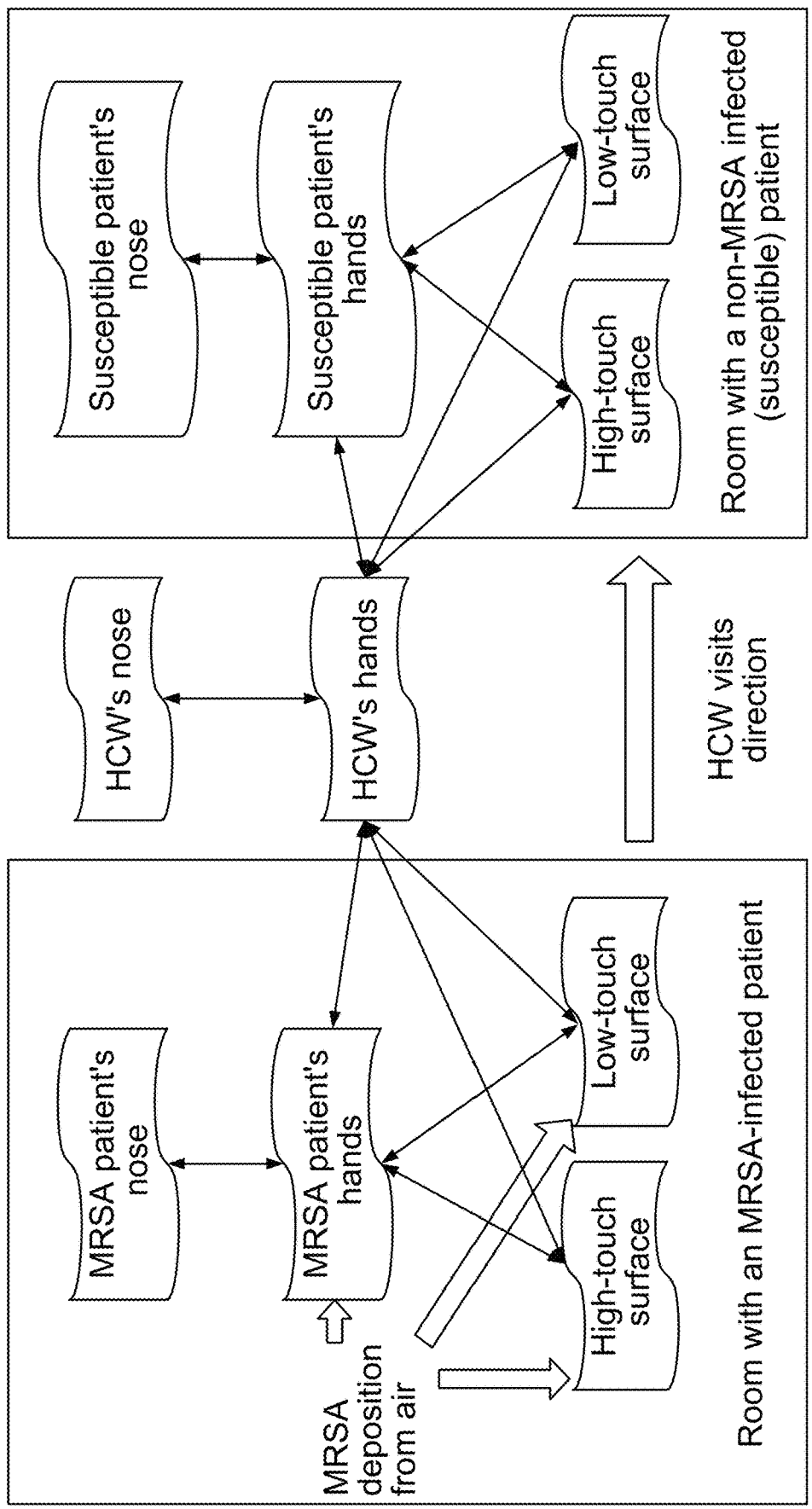
FIG. 1 depicts some of the ways pathogens can propagate through a hospital via the noses and hands of patients and health care workers, as well as low and high touch surfaces.
Figure 2:
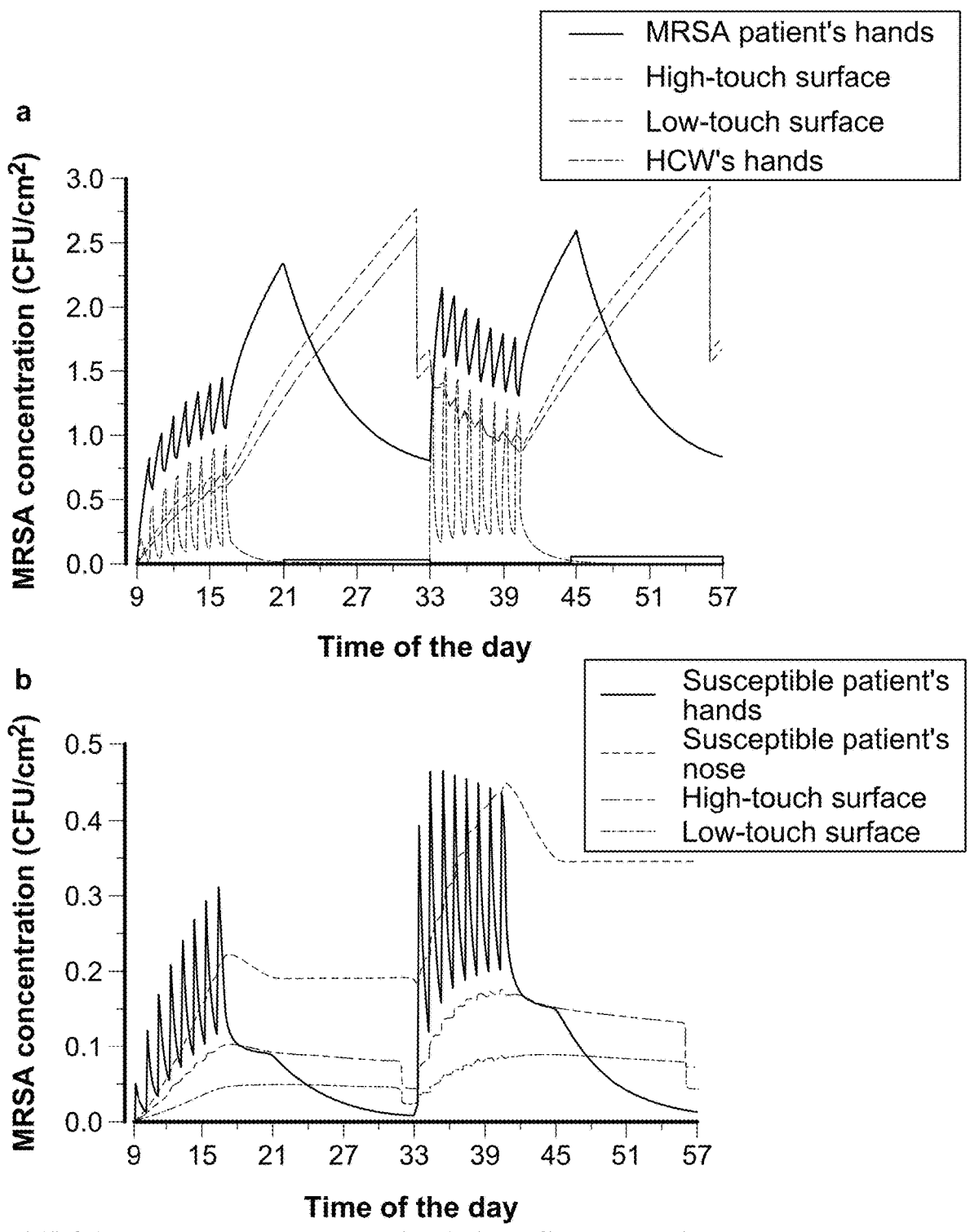
FIG. 2 depicts an image of two charts from the Lei study showing the effect of wiping visibly clean surfaces.
Figure 4:
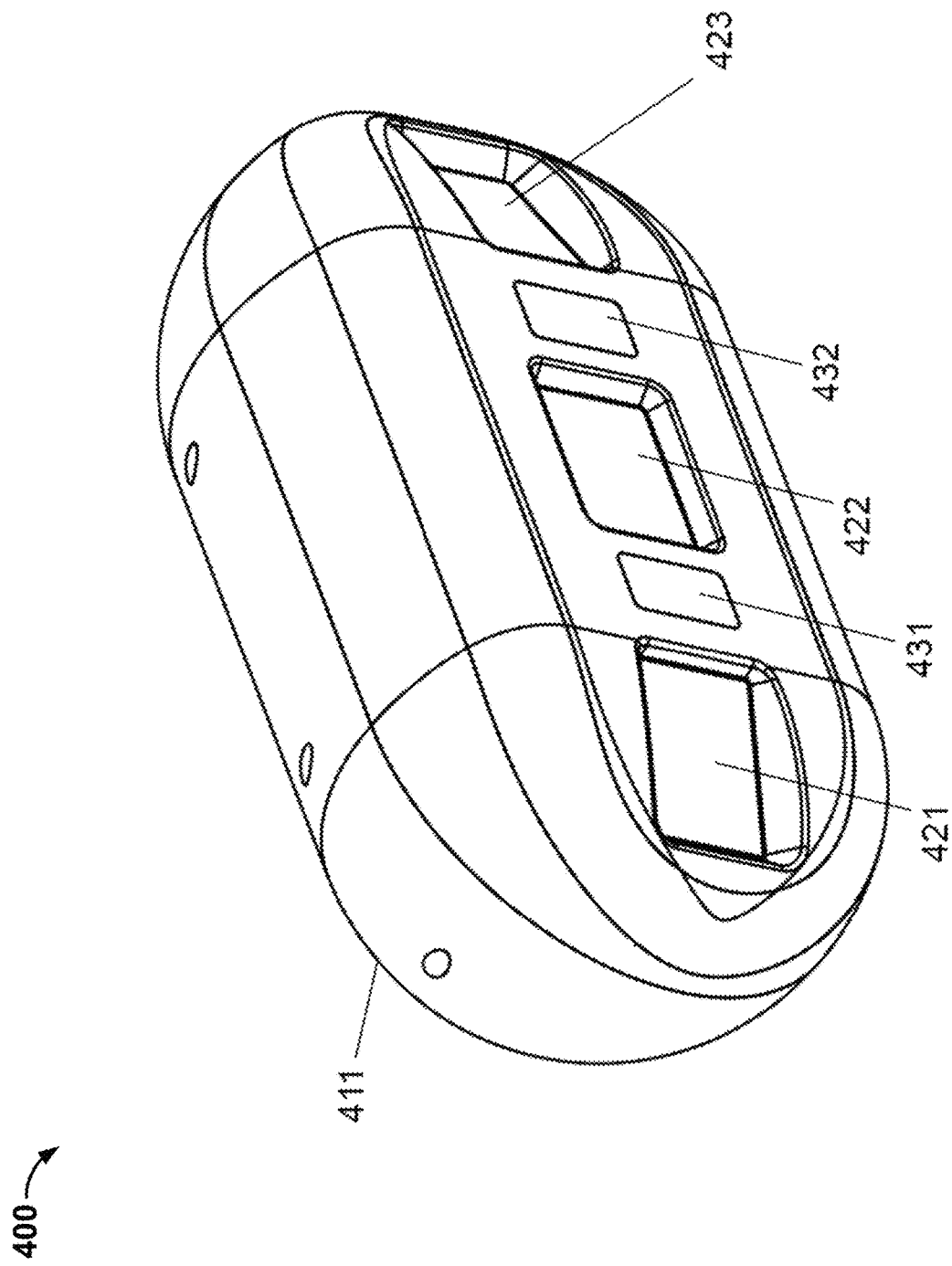
FIG. 4 is a diagram illustrating a device for continuous disinfection of human occupied space in accordance with some embodiments.

FIG. 4 is a diagram illustrating a device for continuous disinfection of human occupied space in accordance with some embodiments. In the example shown, device 400 includes enclosure 411, UV lamps 421, 422, and 423, and camera sensors 431 and 432. Although FIG. 4 depicts device 400 having three UV lamps, device 400 may include 1:n UV lamps. Although FIG. 4 depicts device 400 having two camera sensors, device 400 may include 1:n camera sensors.

In some embodiments, UV lamps 421, 422, and 423 are Ushio B1 narrow beam modules. These modules, produced by Ushio, are filtered KrC1 excimer lamps with a field of irradiance of 60 degrees, input power of 11W, and lamp voltage of 4-6V. UV output at the center of irradiance at 1m is 14uW/cm/\2. Other types of lamps may be used for UV lamps 421, 422, and 423. UV lamps 421, 422, and 423 may be battery powered, plugged into a wall outlet, powered via power over Ethernet, or powered by any other power source.

In some embodiments, camera sensors 431 and 432 are Seeed Studio IMX219-160 8MP cameras with a 30 frames/s frame rate and a field of view of 160 degrees. Other types of camera sensors having different frame rates and field of views may be used. Camera sensor 431 may have a different frame rate and/or a different field of view than camera sensor 432. A single camera sensor can be used to detect and identify people, and two camera sensors can be used on a device to operate stereoscopically and determine coordinates of occupants in a space. A person may be identified based on one or more characteristics, such as the detection of a face, gait, body shape, temperature, or other characteristic. In some embodiments, camera sensors 431 and 432 include the ability to function in the dark, using, for example, infrared light.

In some embodiments, other or additional means are used to detect the presence of people within a space. One such means may be a carbon dioxide sensor that is included within UV device 400 or as an independent device. The carbon dioxide sensor can detect CO2 within the breaths of people. The presence of one or more people may be detected in the event an output of the carbon dioxide sensor is greater than or equal to a carbon dioxide threshold.

Another means of detecting the presence of people within a space may be a thermal sensor or infrared sensor (PIR) that is included within UV device 400 or as an independent device. The thermal or infrared sensor can detect heat emerging from the bodies of people. The presence of one or more people may be detected in the event an output of the thermal sensor or infrared sensor is greater than or equal to a thermal threshold or an infrared threshold.

If a sensor detects the presence of one or more people and the UV lamps 421, 422, 423 are not on, device 400 may turn on the UV lights subject to the presence of people.

The UV lamps of device 400 may have an "on state" and an "off state." An irradiance of light received by a person from the UV light outputted by device 400 may be adjusted based on the number of the UV lamps 421, 422, 423 that are on. In some embodiments, all of the UV lamps 421, 422, 423 have an "on state" when device 400 is operating. In some embodiments, at least two of the UV lamps 421, 422, 423 have an "on state" when device 400 is operating. In some embodiments, at least one of the UV lamps 421, 422, 423 has an "on state" when device 400 is operating. The UV lamps of device 400 have an "off state" when UV lamps 421, 422, 423 are off.

Each of the UV lamps 421, 422, 423 has a corresponding field of illumination. In some embodiments, the field of illumination associated with a UV lamp overlaps with the field of illumination associated with at least one other UV lamp. In some embodiments, the field of illumination associated with a UV lamp does not overlap with the field of illumination associated with any of the other lamps of device 400. Different levels of light can be emitted by different UV lamps depending on whether or not their field of illumination includes persons. For UV lamps for which their field of illumination does not include one or more people, the defined limit of UV light for people can be exceeded; for lamps with fields that include one or more people, the limit is adhered to.

In some embodiments, device 400 includes an ozone sensor. In some embodiments, an ozone sensor may be installed in a space that includes device 400 and is in communication with device 400. The ozone sensor is configured to detect ozone concentrations within a space, such as space 600. In response to a defined ozone threshold concentration being detected by the ozone sensor, device 400 may reduce the UV light emitted by one or more of the UV lamps 421, 422, 423 until the ozone concentration decreases to a predetermined level where the UV light emission can be increased. The ozone can be removed by a HVAC system or decomposed on its own where no air circulation is present. Ozone destruction devices may be included in the ecosystem of devices. These ozone destruction devices can be used to suppress the ozone concentration actively.

Figure 5:
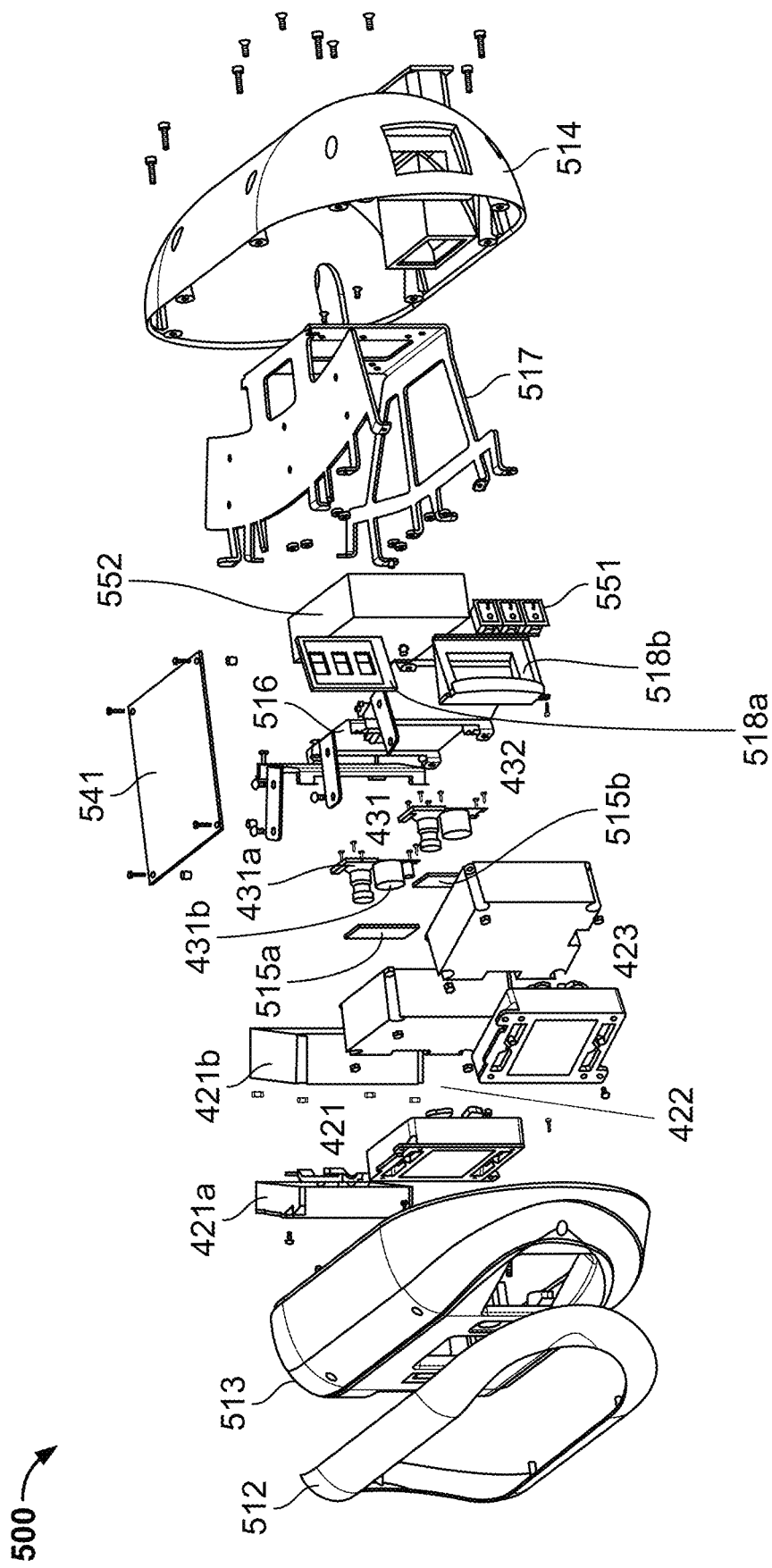
FIG. 5 is an oblique view illustrating a wire diagram of an exploded view of a device for continuous disinfection of human occupied space in accordance with some embodiments.

FIG. 5 is an oblique view 500 illustrating a wire diagram of an exploded view of device 400 in accordance with some embodiments. The functional components of device 400 include: (1) UV lamps 421, 422, and 423; (2) camera sensors 431 and 432; (3) controller 541; and (4) power system 551 and 552. FIG. 5 shows the two major parts of the UV lamps. For example, UV lamp 421 comprises bulb 421a and inverter 421b, which provides power for the bulb. Similarly, each camera sensor comprises two major parts. For example, camera sensor 431 comprises infrared camera 431a and light source 431b.

The power system comprises switch 551 and switched mode power supply (SMPS) 552. Controller 541 comprises one or more processors, random access memory, persistent memory, and communication capabilities.

Device 400 encloses the foregoing functional components in order to physically support, as well as protect them from dust and other substances that could interfere with their functioning. The enclosing and supporting parts include front band 512, front canopy 513, back canopy 514, camera sensor covers 515a and 515b, subframe 516, mainframe 517, and switch holder 518a and switch mount plate 518b. Subframe 516 secures the UV lamps and camera sensors. Mainframe 517 secures controller 541, SMPS 552 as well as subframe 516. Front band 512, front canopy 513, and back canopy 514 secures all of the foregoing.

The foregoing enclosing parts of device 400 can be made of any materials strong, yet light enough, to enable the core functions of the enclosure: securing the functional components, serving without impeding their function, and enabling the device to be readily mounted in any configuration. These materials include, without limitation, one or more of polyethylene, polyvinyl chloride, polypropylene, or metals such as aluminum or stainless steel.

Figure 6:
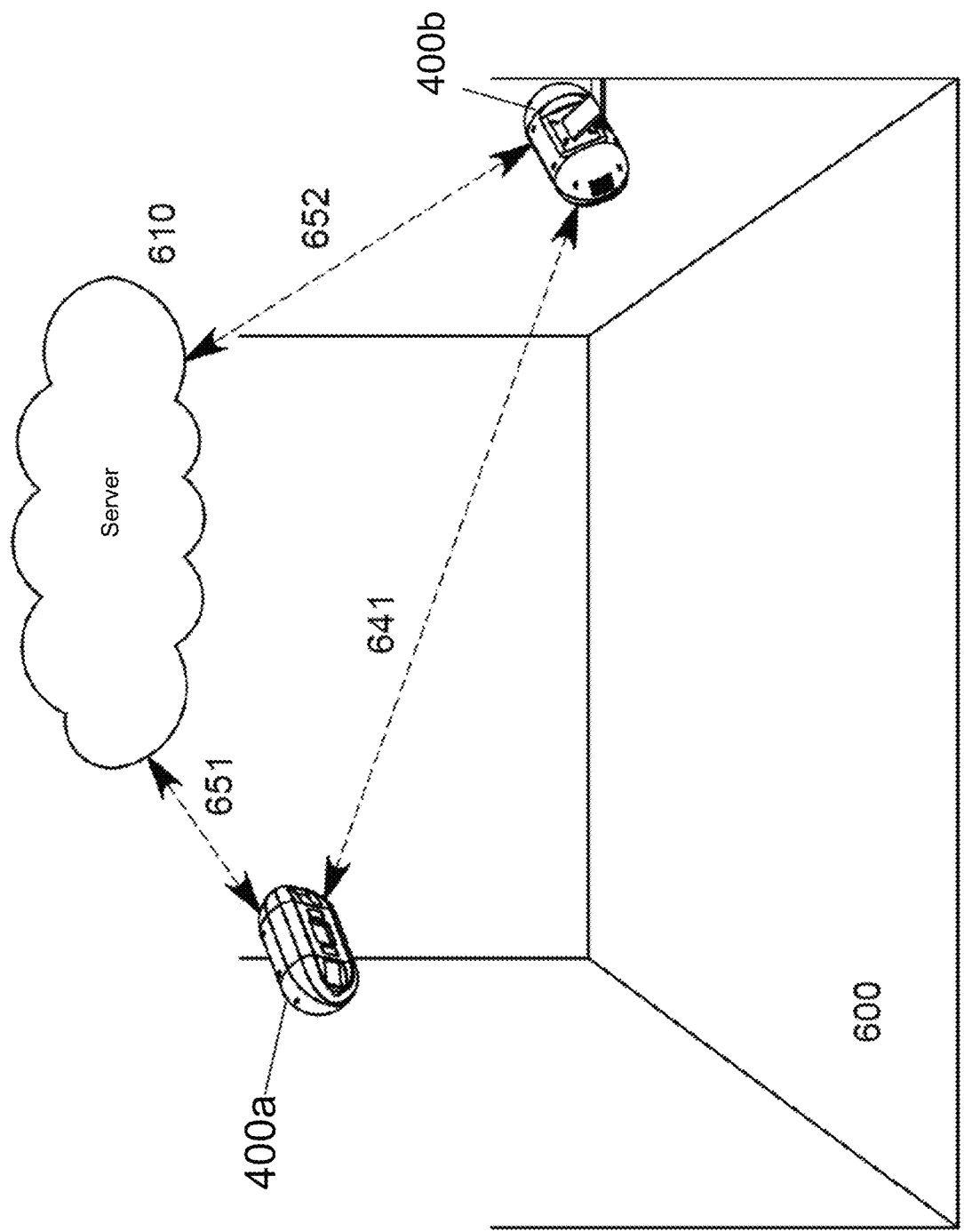
FIG. 6 is a diagram illustrating two devices within a space communicating with each other and with a server in accordance with some embodiments.

FIG. 6 is a diagram illustrating two devices within a space communicating with each other and with server 610 in accordance with some embodiments. FIG. 6 shows a space 600 in which two devices, 400a and 400b, are mounted in opposite corners of space 600, in elevated positions. Server 610 is located locally, or remotely on a network such as the Internet. Devices 400a and 400b may each communicate with server 610 via data transmission paths 651 and 652, respectively. Any sensor housed within a device 400a, 400b may communicate data to server 610 over data transmission paths 651, 652, respectively. Device 400a and 400b may also communicate directly with each other via data transmission path 641. Any sensor housed within device 400a may communicate data to any sensor housed within device 400b over data transmission path 641, and vice versa. Device 400a or device 400b may communicate with one or more other devices that are located in different spaces through a cloud network that includes server 610.

Local communications between devices 400a and 400b, as well as between each of device 400a and 400b with local server 610 may be performed by wireless or wired technologies known in the art, for example, one or more of Ethernet, WiFi, and Bluetooth.

Remote communication between each of device 400a and 400b with remote server 610 is performed by wireless technologies known in the art, for example, cellular and Internet.

One class of information communicated by one or more of device 400a and 400b to server 610 is data such as UV Level received by occupants, be it individuals identified by facial recognition or by wearables or simply people identified as mobile or static. Nurses, doctors (all healthcare workers) and visitors are considered to be mobile occupants. A mobile occupant irradiance threshold or a mobile occupant dose threshold may be established for mobile occupants. For example, the mobile dose occupant threshold may be established such that mobile occupants are not be exposed to greater than 20mj/cm^2 in 15 minutes. Patients are considered to be static occupants. A patient irradiance threshold or a patient dose threshold may be established for patients. For example, the patient dose threshold may be established such that patients' faces are not exposed to greater than 161mj/cm^2 over 8 hours. The light sources from all devices either co-located or independent will be controlled to maintain these UV Levels.

One or more of devices 400a and 400b communicates total light energy delivered to the room or various items within the room identified by machine vision (for example, heat map data). In some embodiments, this device-to-server communication includes possible pathogen reductions based on heat map and light UV Levels attained on surfaces (e.g., IV pump). In some embodiments, device 400a or 400b has pathogen sensing technology and communicates pathogens sensed and or pathogen loads to server 610 which then, in turn, communicates light cycle profiles to be run. For example, an IV pump may be associated with a cycle profile to reduce specific microorganisms located on the surface of the IV pump. In some embodiments, the one or more devices 400a, 400b implement machine vision to identify various objects. The one or more devices 400a, 400b may be trained to identify various objects. Some objects of interest may be disinfected with higher doses of light when people are not within the field of illumination associated with a UV light source or when a space in which the one or more devices 400a, 400b are installed is empty.

Depending on the use case, server 610 communicates different light cycle profiles to be run by one or more of devices 400a and 400b. As well, server 610 communicates updates to light cycle profiles or new profiles. In some embodiments, a controller of device 400a or device 400b turns on respective UV lamps 421, 422, and 423 according to a life cycle profile. The life cycle may be used to extend a lamp life associated with UV lamps 421, 422, 423. The life cycle profile may indicate a frequency (e.g., hourly, daily, weekly, etc.) at which the respective UV lamps 421, 422, 423 are turned on. UV lamps 421, 422, 423 have a corresponding lifetime. The environment in which a device 400a, 400b is located may be a low traffic area, a medium traffic area, or a high traffic area. The frequency at which the respective UV lamps 421, 422, 423 are turned on when the presence of one or more people is not detected may depend on the type of traffic area of device 400. A low traffic area may correspond to an environment that has a number of visitors less than a first threshold during a first duration. A medium traffic area may correspond to an environment that has a number of visitors that is greater than or equal to the first threshold and less than a second threshold during the first duration. A high traffic area may correspond to an environment that has a number of visitors that is greater than or equal to the second threshold during the first duration.

The profile may indicate a schedule when the respective UV lamps 421, 422, 423 are to be turned on. For example, UV lamps 421, 422, 423 may be scheduled to turn on at the close of business and/or before a business is to open for the day. The life cycle profile may associate a space with a particular type of space (e.g., boardroom). The particular type of space may correspond to a particular type of traffic area (e.g., low, medium, or high). As a result, the UV lamps 421, 422, 423 may be turned on/off according to the type of traffic area that is associated with the space.

In the event that two or more UV devices 400a and 400b are in the same room or space, they would need to operate from a global coordinate system whereby the same people are not identified multiple times by different devices. The angle and orientation are communicated so that fields of illumination that overlap can be accounted for and the lights controlled accordingly on one or more devices to keep all of the occupants under the maximum allowable UV Level.

Figure 7:
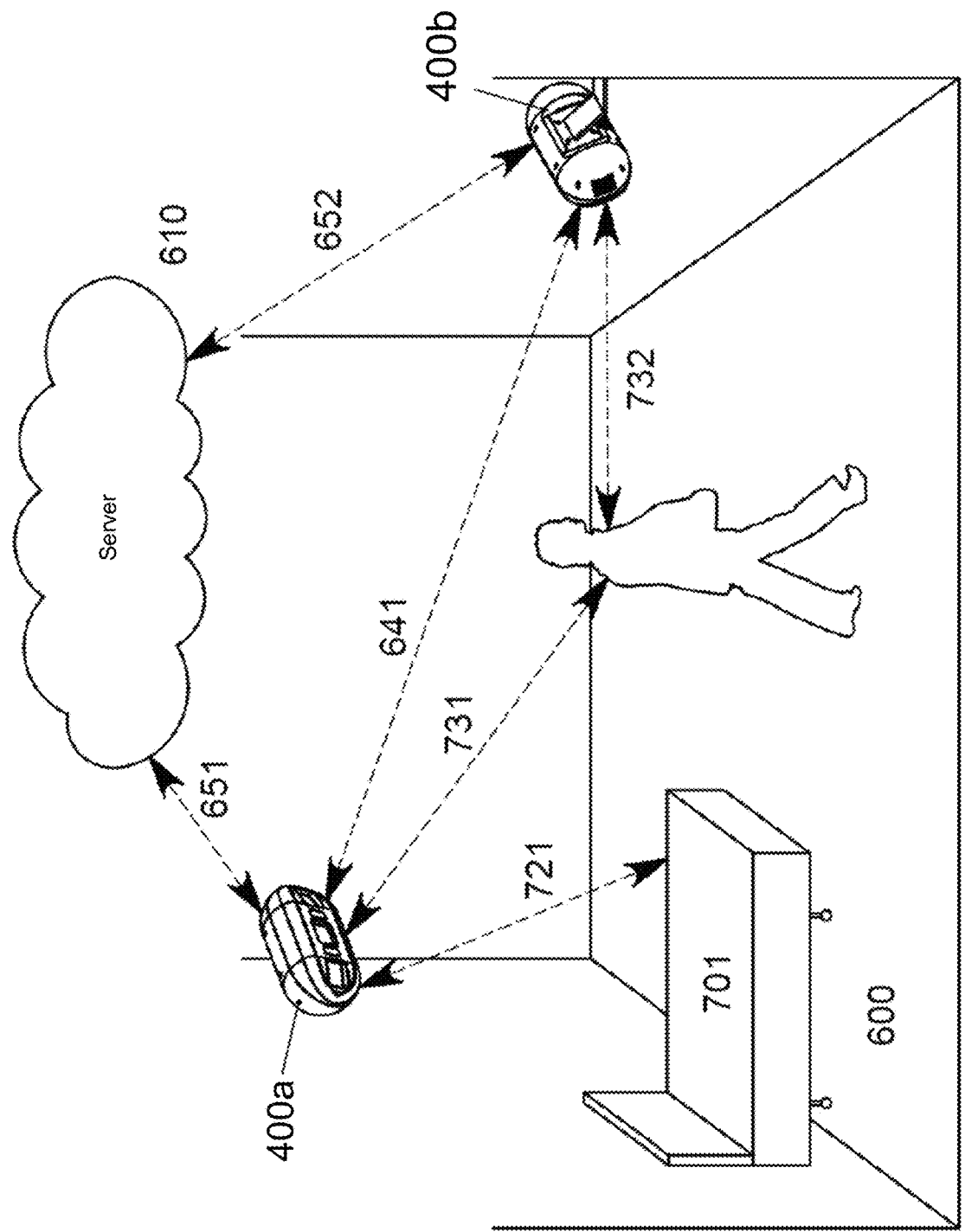
FIG. 7 is a diagram illustrating two devices within a space communicating with each other and with a server, while shining UV light and while sensing the presence of a human in accordance with some embodiments.

FIG. 7 is a diagram illustrating two devices within a space communicating with each other and with server 610, while emitting UV light and while sensing the presence of a human in accordance with some embodiments. As with the previous figures, FIG. 7 includes devices 400a and 400b, space 600, cloud 610, data transmission paths 651 and 652 (between devices 400a and 400b and server 610), and data transmission path 641 (between devices 400a and 400b directly).

FIG. 7 further shows bed 701 and person 732. Such elements are common in hospital rooms, hotel rooms, therapeutic centers, and many more such spaces. UV light 721 is generated by the first UV lamp of device 400a and serves to kill pathogens present on bed 701. Camera sensors embedded in device 400a and 400b, have respective fields of view 731 and 732, which detect the presence of a person. In some embodiments, these sensors also detect the location of the person within space 600.

Figure 8A:
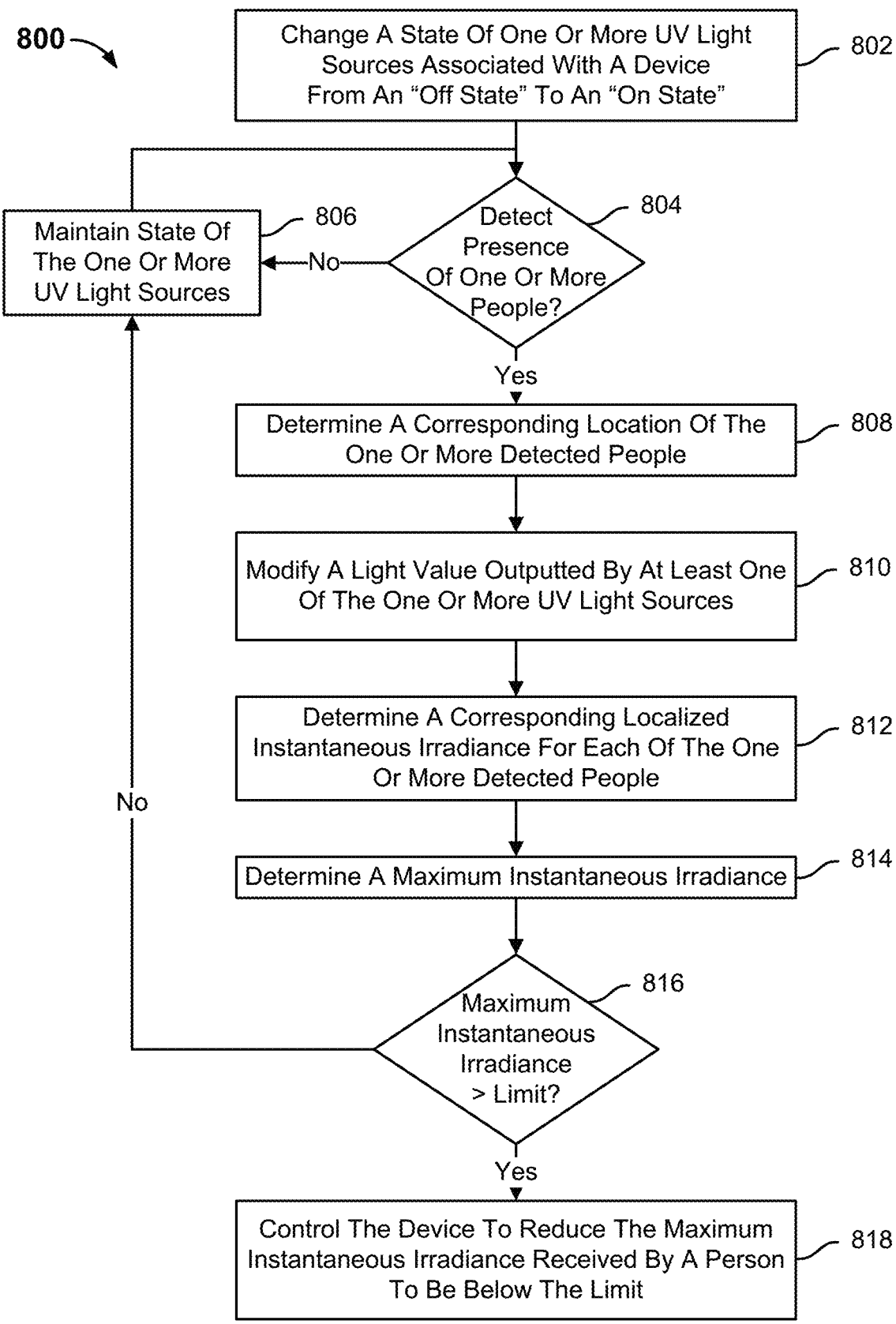
FIG. 8A is a flow diagram illustrating a process for minimizing UV exposure to people in accordance with some embodiments.

FIG. 8A is a flow diagram illustrating a process for minimizing UV exposure to people in accordance with some embodiments. Process 800 may be implemented by a device, such as devices 400a, 400b.

At 802, a state of one or more UV light sources associated with a device is changed from an "off state" to an "on state." The device may include 1:n UV light sources. In some embodiments, a UV light source is a UV lamp. In some embodiments, a UV light source is an LED light. In some embodiments, a controller of the device changes a state for all of the one or more UV light sources from the "off state" to the "on state" by sending respective signals to inverters associated with the one or more UV light sources (e.g., inverters 421*b*, 422*b*, 423*b*). In some embodiments, the controller of the device changes a state for some of the one or more UV light sources from the "off state" to the "on state" by sending respective signals to inverters associated with some of the one or more UV light sources. The controller of the device may turn on the one or more UV light sources according to a life cycle policy. The one or more UV light sources associated with the device output a first light value. In some embodiments, the first light value outputted by the one or more UV light sources associated with the device causes an irradiance of 40 uW/cm/\2 to be received on surfaces within a space when the UV light source outputs UV light having a wavelength of 222 nm. The one or more UV light sources may output different light values that cause different irradiance values to be received on surfaces within a space. The one or more UV light sources may output light using a different UV wavelength.

At 804, it is determined whether a presence of one or more people is detected within the space. The device may include one or more sensors to detect the presence of one or more people within the space. The one or more sensors may include one or more camera sensors (e.g., camera sensors 431 or camera sensor 432), radar, lidar, time-of-flight, a motion sensor, a thermal sensor, an infrared sensor, a carbon dioxide sensor, and/or a combination thereof.

In response to a determination that the presence of one or more people is not detected within the space, process 800 proceeds to 806 where a state of the one or more UV light sources is maintained. In response to a determination that a presence of one or more people is detected within the space, process 800 proceeds to 808.

At 808, a corresponding location of the one or more detected people is determined. In some embodiments, the corresponding location of the one or more detected people is determined by one or more camera sensors of the device. The one or more camera sensors of the device may determine corresponding coordinates of the one or more detected people relative to the device. The determined coordinates may correspond to a head, a torso, or other body part associated with a detected person. The corresponding coordinates may be determined using a Cartesian coordinate system (x, y, z), a cylindrical coordinate system (p, φ, z), a spherical coordinate system (r, Θ, Φ), or any other type of coordinate system.

In some embodiments, the corresponding location of the one or more detected people is inferred from one or more sensors of the device. For example, the device may include a carbon dioxide sensor that detects carbon dioxide in a space. The carbon dioxide may output a value that indicates the presence of one or more people in a particular area of the space.

At 810, UV light outputted by at least one of the one or more UV light sources is modified. Irradiance can be maximized on other surfaces within a space as long as people detected within the space are maintained under a prescribed irradiance. The UV light outputted by the one or more UV light sources is modified to ensure that the UV light delivered to the one or more detected people does not exceed a limit.

Each UV light source has a corresponding field of illumination. The controller of the device may determine which of the corresponding fields of illumination include people based on the determined corresponding locations of the one or more detected people. The controller determines the one or more UV light source(s) that correspond to the one or more fields of illumination that include one or more people. For a UV light source that does not correspond to a field of illumination that includes one or more people, the controller maintains an output of the UV light source to be the first light value.

In some embodiments, the one or more sensors of the device detect a face of a person. For a UV light source that corresponds to a field of illumination that includes at least one face of a person, the controller modifies an output of the UV light source from a first light value to a second light value. For example, the second light value may cause an irradiance of 5.59 uW/cm/\2 or less to be received by the person when the UV light source outputs UV light having a wavelength of 222 nm. The second light value may cause other irradiance values to be received by the person when the UV light source outputs UV light having a wavelength of 222 nm. The second light value may be different for different UV wavelengths. The desired irradiance received by the person when a face is detected may be different for different UV wavelengths.

In some embodiments, the one or more sensors of the device do not detect a face of a person. For a UV light source that corresponds to a field of illumination that includes at least one person without a face being detected, the controller modifies an output of the UV light source from a first light value to a second light value. For example, the second light value may cause an irradiance of 16.35 uW/cm/\2 or less to be received by the person when the UV light source outputs UV light having a wavelength of 222 nm. The second light value may cause other irradiance values to be received by the person when the UV light source outputs UV light having a wavelength of 222 nm. The second light value may be different for different UV wavelengths. The desired irradiance received by the person when a face is not detected may be different for different UV wavelengths.

A wavelength of light outputted by the UV light source may be any wavelength in the UV spectrum (e.g., 100 nm-400 nm). In one embodiment, the wavelength is 222 nm.

At 812, a corresponding localized instantaneous irradiance is determined for each of the one or more detected people. After the device is installed in a particular space, the device may be calibrated by measuring the localized instantaneous irradiance at a plurality of locations in the particular space. The localized instantaneous irradiance measured at the plurality of locations may be stored in a lookup table or other type of data structure.

In some embodiments, the lookup table or other type of data structure is stored in a local memory or storage associated with the device. The controller of the device may utilize the lookup table or other type of data structure and the corresponding location of the one or more detected people to determine the corresponding localized instantaneous irradiance for each of the one or more detected people.

In some embodiments, the lookup table or other type of data structure is stored in a remote server (e.g., server 610). The device may provide the remote server the corresponding location of the one or more detected people and request the remote server to provide the corresponding localized instantaneous irradiance for each of the one or more detected people based on the provided corresponding location of the one or more detected people. In response to the request, the server may provide the corresponding localized instantaneous irradiance for each of the one or more detected people based on the corresponding location of the one or more detected people.

At 814, a maximum instantaneous irradiance among the corresponding localized instantaneous irradiance associated with each of the one or more people is determined.

At 816, it is determined whether the maximum instantaneous irradiance is greater than a limit. In some embodiments, the limit is a safety limit. An example of a safety limit is an irradiance of 5.59 uW/cm/\2 when the face of a person is detected. Another example of a safety limit is an irradiance of 16.35 uW/cm/\2 when the face of a person is not detected. Other irradiance values may be used as a safety limit. In some embodiments, the safety limit is associated with an allowable safe UV Level limit for skin. In some embodiments, the safety limit is associated with an allowable safe UV Level limit for eyes.

In response to a determination that the maximum instantaneous irradiance is greater than the limit, process 800 proceeds to 818. In response to a determination that the maximum instantaneous irradiance is not greater than the limit, process 800 proceeds to 806.

At 818, the device is controlled to reduce the maximum instantaneous irradiance received by a person to be below the limit.

In some embodiments, the state of all of the one or more UV light sources associated with the device is changed from the "on state" to the "off state" to reduce the maximum instantaneous irradiance received by a person to be below the limit. The one or more UV light sources associated with the device may remain in the "off state" for a particular time interval Ti. Process 800 may be repeated after an expiration of the particular time interval Ti. In some embodiments, process 800 is repeated according to a life cycle policy associated with the device.

In some embodiments, the device includes a plurality of UV light sources and a state of some of the one or more UV light sources associated with the device is changed from the "on state" to the "off state" to reduce the maximum instantaneous irradiance received by a person to be below the limit. Each UV light source has a corresponding field of illumination. The field of illumination associated with a first UV light source may partially overlap with the field of illumination associated with a second UV light source. A person may be located within the field of illumination overlap. As a result, the localized instantaneous irradiance received by the person may be greater than the limit. The controller may turn off the first UV light source and maintain a state of the second UV light source. This may cause the localized instantaneous irradiance received by the person to be less than the limit.

In some embodiments, an maximum instantaneous irradiance received by a person is reduced to be below the limit by actuating one or more occlusion devices to cover the one or more UV light sources. For example, each of the UV lamps 421, 422, 423 may be associated with a corresponding occlusion device (e.g., a shutter). In some embodiments, the occlusion devices associated with all of the UV light sources of the device are actuated to reduce the maximum instantaneous irradiance received by the person to be below the limit. In some embodiments, the occlusion devices associated with some of the UV light sources of the device are actuated to reduce the maximum instantaneous irradiance received by the person to be below the limit.

Figure 8B:
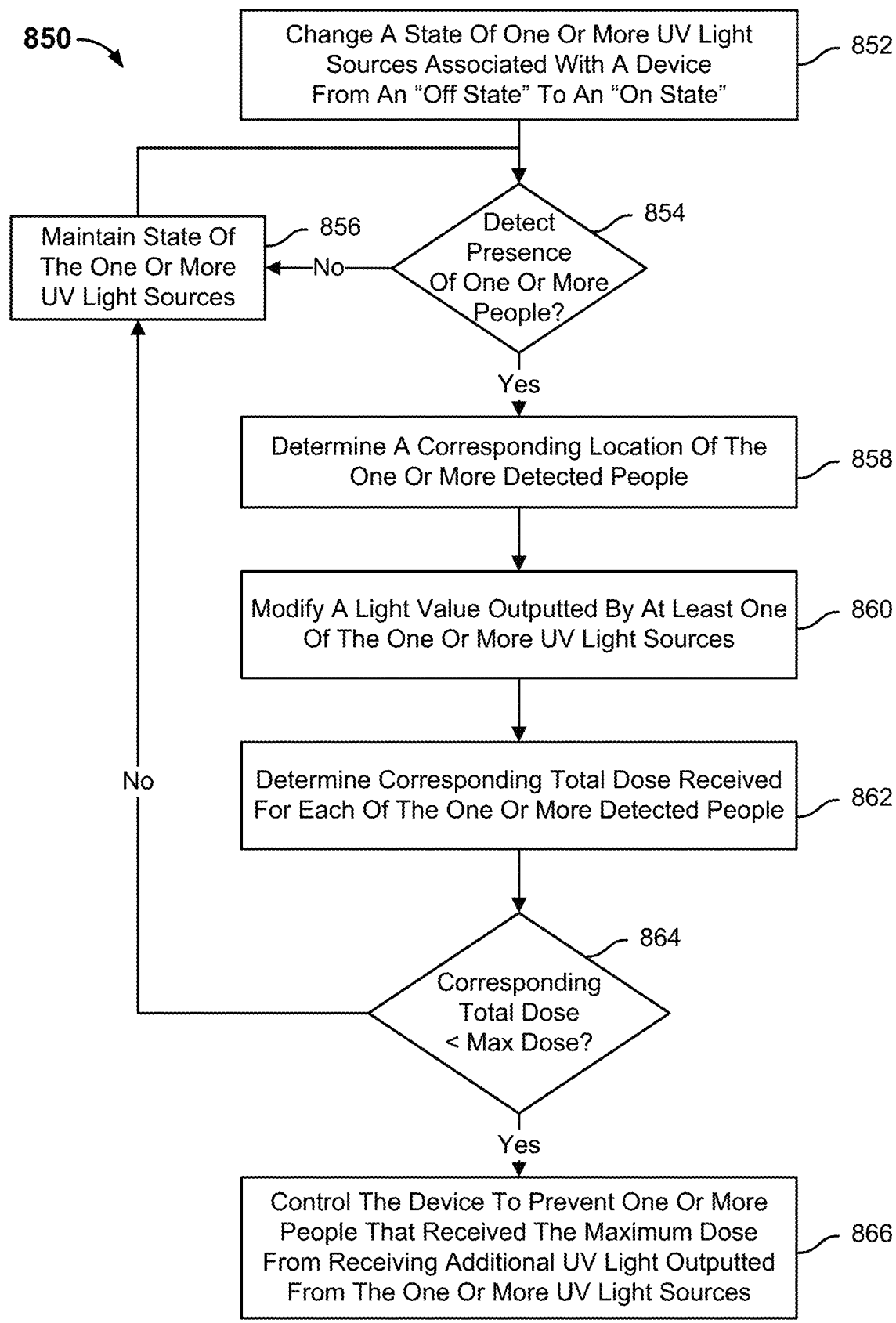
FIG. 8B is a flow diagram illustrating a process for minimizing UV exposure to people in accordance with some embodiments.

FIG. 8B is a flow diagram illustrating a process for minimizing UV exposure to people in accordance with some embodiments. Process 8B may be implemented by a device, such as devices 400a, 400b. Process 850 may be implemented in parallel or separately from process 800.

At step 852, a state of one or more UV light sources associated with a device is changed from an "off state" to an "on state." In some embodiments, a controller of the device changes a state for all of the one or more UV light sources from the "off state" to the "on state" by sending respective signals to inverters associated with the one or more UV light sources (e.g., inverters 421b, 422b, 423b). In some embodiments, the controller of the device changes a state for some of the one or more UV light sources from the "off state" to the "on state" by sending respective signals to inverters associated with some of the one or more UV light sources. The controller of the device may turn on the one or more UV light sources according to a life cycle policy. The one or more UV light sources associated with the device output a first light value.

In some embodiments, the first light value outputted by the one or more UV light sources associated with the device causes an irradiance of 16.35 uW/cm/\2 to be received on surfaces within a space when the UV light source outputs UV light having a wavelength of 222 nm. The one or more UV light sources may output different light values that cause different irradiance values to be received on surfaces within a space. The one or more UV light sources may output light using a different UV wavelength.

At 854, it is determined whether a presence of one or more people is detected within the space. The device may include one or more sensors to detect the presence of one or more people within the space. The one or more sensors may include one or more camera sensors (e.g., camera sensors 431 or camera sensor 432), radar, lidar, time-of-flight, a motion sensor, a thermal sensor, an infrared sensor, a carbon dioxide sensor, and/or a combination thereof.

In response to a determination that the presence of one or more people is not detected within the space, process 850 proceeds to 856 where a state of the one or more UV light sources is maintained. In response to a determination that a presence of one or more people is detected within the space, process 850 proceeds to 858.

At 858, a corresponding location of the one or more detected people is determined. In some embodiments, the corresponding location of the one or more detected people is determined by one or more camera sensors of the device. The one or more camera sensors of the device may determine corresponding coordinates of the one or more detected people relative to the device. The determined coordinates may correspond to a head, a torso, or other body part associated with a detected person. The corresponding coordinates may be determined using a Cartesian coordinate system (x, y, z), a cylindrical coordinate system (p, cp, z), a spherical coordinate system (r, 0, 1), or any other type of coordinate system.

In some embodiments, the corresponding location of the one or more detected people is inferred from one or more sensors of the device. For example, the device may include a carbon dioxide sensor that detects carbon dioxide in a space. The carbon dioxide may output a value that indicates the presence of one or more people in a particular area of the space.

At 860, UV light outputted by at least one of the one or more UV light sources is modified. The UV light outputted by the one or more UV light sources is modified to ensure that the UV light delivered to the one or more detected people does not exceed a limit.

Each UV light source has a corresponding field of illumination. The controller of the device may determine which of the corresponding fields of illuminations include people based on the determined corresponding locations of the one or more detected people. The controller determines the one or more UV light source(s) that correspond to the one or more fields of illumination that include one or more people. For a UV light source that does not correspond to a field of illumination that includes one or more people, the controller maintains an output of the UV light source to be the first light value.

In some embodiments, the one or more sensors of the device detect a face of a person. For a UV light source that corresponds to a field of illumination that includes at least one face of a person, the controller modifies an output of the UV light source from a first light value to a second light value. For example, the second light value may cause an irradiance of 5.59 uW/cm$^\wedge$2 or less to be received by the person when the UV light source outputs UV light having a wavelength of 222 nm. The second light value may cause other irradiance values to be received by the person when the UV light source outputs UV light having a wavelength of 222 nm. The second light value may be different for different UV wavelengths. The desired irradiance received by the person when a face is detected may be different for different UV wavelengths.

In some embodiments, the one or more sensors of the device do not detect a face of a person. For a UV light source that corresponds to a field of illumination that includes at least one person without a face being detected, the controller modifies an output of the UV light source from a first light value to a second light value. For example, the second light value may cause an irradiance of 16.35 uW/cm$^\wedge$2 or less to be received by the person when the UV light source outputs UV light having a wavelength of 222 nm. The second light value may cause other irradiance values to be received by the person when the UV light source outputs UV light having a wavelength of 222 nm. The second light value may be different for different UV wavelengths. The desired irradiance received by the person when a face is not detected may be different for different UV wavelengths.

A wavelength of light outputted by the UV light source may be any wavelength in the UV spectrum (e.g., 100 nm-400 nm). In one embodiment, the wavelength is 222 nm.

At 862, a corresponding total dose of UV light received by each of the one or more detected people is determined. A data structure may store a corresponding total dose of UV light received by each of the one or more detected people while the one or more detected people are in the space. The data structure may be stored by the device or a remote server.

The total dose received by a person is a cumulative irradiance received by the person over a period of time. In some embodiments, the data structure stores a corresponding total dose of UV light received by each of the one or more detected people over a particular period of time, regardless of which space a person is located. For example, a person may be located at a first space for a first period of time, a second space for a second period of time, . . . , and an nth space for an nth period of time. The total dose for the person is the sum of the total dose received at the first space during the first period of time, the total dose received at the second space during the second period of time, . . . , and the total dose received at the nth space for the nth period of time.

In some embodiments, the location of a person between spaces is tracked using facial recognition software. In some embodiments, the location of a person between spaces is tracked based on a wearable device worn by the person. For example, the wearable device may be associated with a unique identifier and broadcast this unique identifier. A device, such as device 400, may receive the unique identifier and associate the unique identifier with a detected person.

The data structure may store the total dose of UV light received by the person across the different spaces over the particular period of time. The controller may update the data structure each time it determines a corresponding localized, instantaneous irradiance for each of the one or more detected people at 812.

At 864, it is determined whether the corresponding total dose of UV light received by each of the one or more people is less than a maximum dose. In response to a determination that the corresponding total dose of UV light received by each of the one or more people is less than the maximum dose, then process 850 proceeds to 856. In response to a determination that the total dose of UV light received by at least one of the one or more people is not less than the maximum dose, then process 850 proceeds to 866.

At 866, the device is controlled to prevent the one or more people that received the maximum dose from receiving additional UV light outputted from the one or more UV light sources.

In some embodiments, a state of at least one of the one or more UV light sources associated with a device is changed from an "on state" to an "off state." Each of the one or more UV light sources associated with the device has a corresponding field of illumination. A person that has received the maximum dose may be in a field of illumination associated with one or more UV light sources. A controller of the device may determine which fields of illumination the person is located in based on the person's determined location. The controller may change the state of the one or more UV light sources corresponding to the determined fields of illumination that include the person that has received the maximum dose to prevent the person from receiving additional UV light outputted by those UV light source(s). In some embodiments, the at least one of the one or more UV light sources is turned off for a time interval Ti.

In some embodiments, the device actuates one or more occlusion devices to cover the one or more UV light sources to prevent the one or more people that received the maximum dose from receiving additional UV light outputted from the one or more UV light sources. For example, each of the UV lamps 421, 422, 423 may be associated with a corresponding occlusion device (e.g., a shutter). In some embodiments, the occlusion devices associated with all of the UV light sources of the device are actuated to prevent the one or more people that received the maximum dose from receiving additional UV light outputted from the one or more UV light sources.

In some embodiments, the occlusion devices associated with some of the UV light sources of the device are actuated (i.e., an occlusion device associated with a UV light source having a field of illumination that includes a person that has received the maximum dose of UV light) to prevent the one or more people that received the maximum dose from receiving additional UV light outputted from the one or more UV light sources.

Figure 9A:
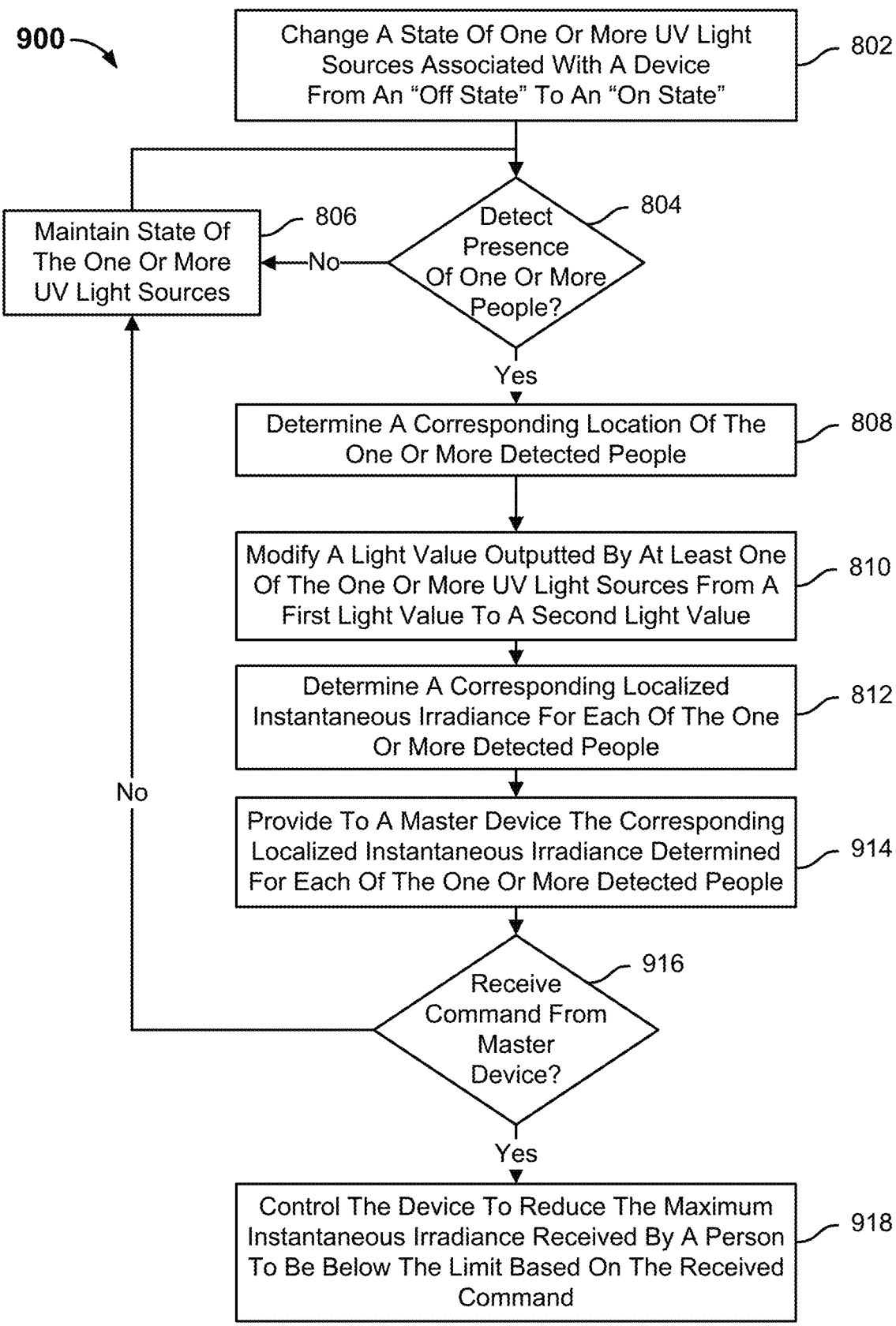
FIG. 9A is a flow diagram illustrating a process for minimizing UV exposure to people in accordance with some embodiments.

FIG. 9A is a flow diagram illustrating a process for minimizing UV exposure to people in accordance with some embodiments. Two or more UV devices may operate in a master-slave relationship. Process 900 may be implemented by one or more slave devices, such as device 400a of FIG. 7.

Process 900 is similar to process 800, except that steps 814, 816, and 818 have been replaced with steps 914, 916, and 918.

At 914, the corresponding localized instantaneous irradiance determined for each of the one or more detected people is provided to a master device. A master device may be device 400b of FIG. 7. The corresponding localized instantaneous irradiance determined for each of the one or more detected people may be provided via a data transmission path, such as data transmission path 641. In other embodiments, the master device is a remote server, such as remote server 610. In some embodiments, determined locations and determined fields of illumination are also provided to the server. In response the remote server may determine the corresponding localized instantaneous irradiance determined for each of the one or more detected people based on the determined locations and the determined fields of illumination.

At 916, it is determined whether a command is received from a master device. The master device may provide a command that indicates the slave device is to reduce the maximum instantaneous irradiance received by a person to be below a limit. In some embodiments, the command is received from another device within the space. For example, device 400a may receive the command from device 400b. In some embodiments, the command is received from a remote server. For example, device 400a or 400b may receive the command from remote server 610.

In response to a determination that a command is not received from the master device, process 900 returns to 806. In response to a determination that a command is received from the master device, process 900 proceeds to 918.

At 918, the device is controlled to reduce the maximum instantaneous irradiance received by a person to be below the limit based on the received command.

In some embodiments, the master device command causes the state of all of the one or more UV light sources associated with the slave device to be changed from the "on state" to the "off state". The one or more UV light sources associated with the slave device may remain in the "off state" for a particular time interval Ti. Process 900 may be repeated after an expiration of the particular time interval Ti. In some embodiments, process 900 is repeated according to a life cycle policy associated with the slave device.

In some embodiments, the slave device includes a plurality of UV light sources and a state of some of the one or more UV light sources associated with the slave device is changed from the "on state" to the "off state." Each UV light source has a corresponding field of illumination. The field of illumination associated with a first UV light source of the slave device may partially overlap with the field of illumination associated with a second UV light source. The second UV light source may be associated with the slave device, a different slave device, or the master device. A person may be located within the field of illumination overlap. As a result, the localized instantaneous irradiance received by the person may be greater than the limit. The controller of the slave device may turn off the first UV light source while a state of the second UV light source is maintained (either by the slave device, the different slave device, or the master device). This may cause the localized instantaneous irradiance received by the person to be less than the limit.

In some embodiments, a maximum instantaneous irradiance received by a person is reduced to be below the limit by actuating one or more occlusion devices to cover the one or more UV light sources. For example, each of the UV lamps 421, 422, 423 may be associated with a corresponding occlusion device (e.g., a shutter). In some embodiments, the occlusion devices associated with all of the UV light sources of the slave device are actuated to reduce the maximum instantaneous irradiance received by the person to be below the limit. In some embodiments, the occlusion devices associated with some of the UV light sources of the slave device are actuated to reduce the maximum instantaneous irradiance received by the person to be below the limit.

Figure 9B:
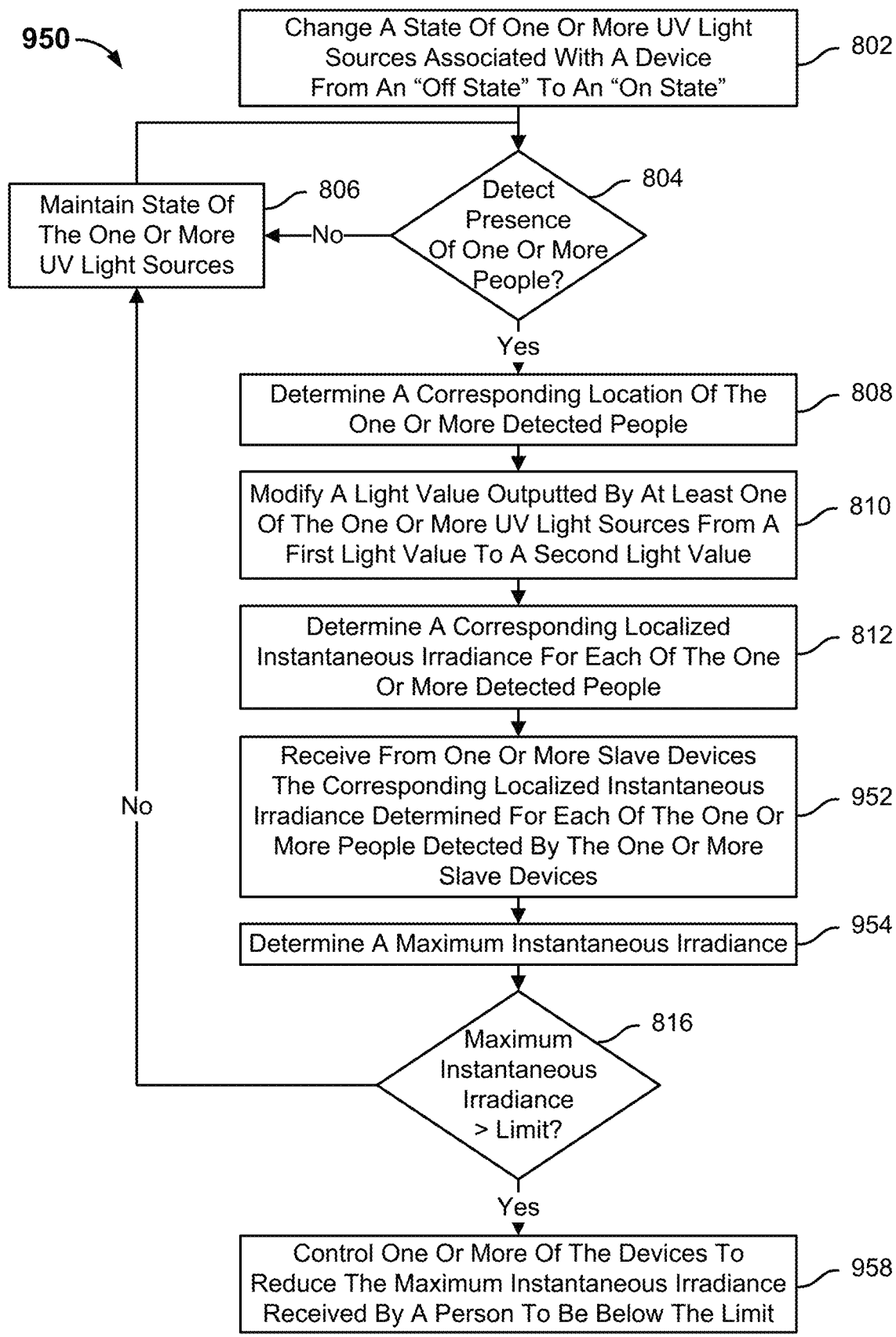
FIG. 9B is a flow diagram illustrating a process for minimizing UV exposure to people in accordance with some embodiments.

FIG. 9B is a flow diagram illustrating a process for minimizing UV exposure to people in accordance with some embodiments. Two or more UV devices may operate in a master-slave relationship. Process 950 may be implemented by a master device, such as device 400b of FIG. 7. Process 950 may operate in parallel with process 900.

Process 950 is similar to process 800, except that steps 814 and 818 have been replaced with steps 952, 954, and 958.

At 952, the corresponding localized instantaneous irradiance determined for each of the one or more people detected by the one or more slave devices is received from the one or more slave devices.

At 954, the master device determines a maximum instantaneous irradiance for one or more people detected within a space using the localized instantaneous irradiance determined by the master device for each of the one or more people detected by the master device and the localized instantaneous irradiance determined by the one or more slave device for each of the one or more people detected by the one or more slave devices. For each person, the master device may add the localized instantaneous irradiances to determine a total instantaneous irradiance for each of the one or more people detected within the space and determine the maximum instantaneous irradiance for the one or more detected within the space based on the determined total instantaneous irradiances.

For example, there may be three people detected within a space. The master device may determine a localized instantaneous irradiance for person 1 to be $I1_m$, a localized instantaneous irradiance for person 2 to be $I2_m$, and a localized instantaneous irradiance for person 3 to be $I3_m$. The master device may have received from a slave device a localized instantaneous irradiance for person 1 to be $I1_s$, a localized instantaneous irradiance for person 2 to be $I2_s$, and a localized instantaneous irradiance for person 3 to be $I3_s$. The master device may determine the total localized instantaneous irradiance for person 1 (I1) to be equal to the sum of $I1_m$ and $I1_s$, the total localized instantaneous irradiance for person 2 (I2) to be equal to the sum of $I2_m$ and $I2_s$, and total localized instantaneous irradiance for person 3 (I3) to be equal to the sum of $I3_m$ and $I3_s$. The maximum instantaneous irradiance among person 1, person 3, and person 3 is the maximum value among I1, I2, and I3.

At 816, the maximum instantaneous irradiance is compared to the limit. In response to a determination that the maximum instantaneous irradiance is not greater than the limit, process 950 proceeds to 806. In response to a determination that the maximum instantaneous irradiance is greater than the limit, process 950 proceeds to 958.

At 958, one or more of the devices are controlled to reduce the maximum instantaneous irradiance received by a person to be below the limit. In some embodiments, the master device controls itself in a manner as described at step 818 of process 800.

In some embodiments, the master device provides to one or more slave devices corresponding commands to reduce the maximum instantaneous irradiance received by a person to be below the limit. In response to receiving the command, a slave device may control itself in a manner as described at step 918 of process 900.

Figure 10:
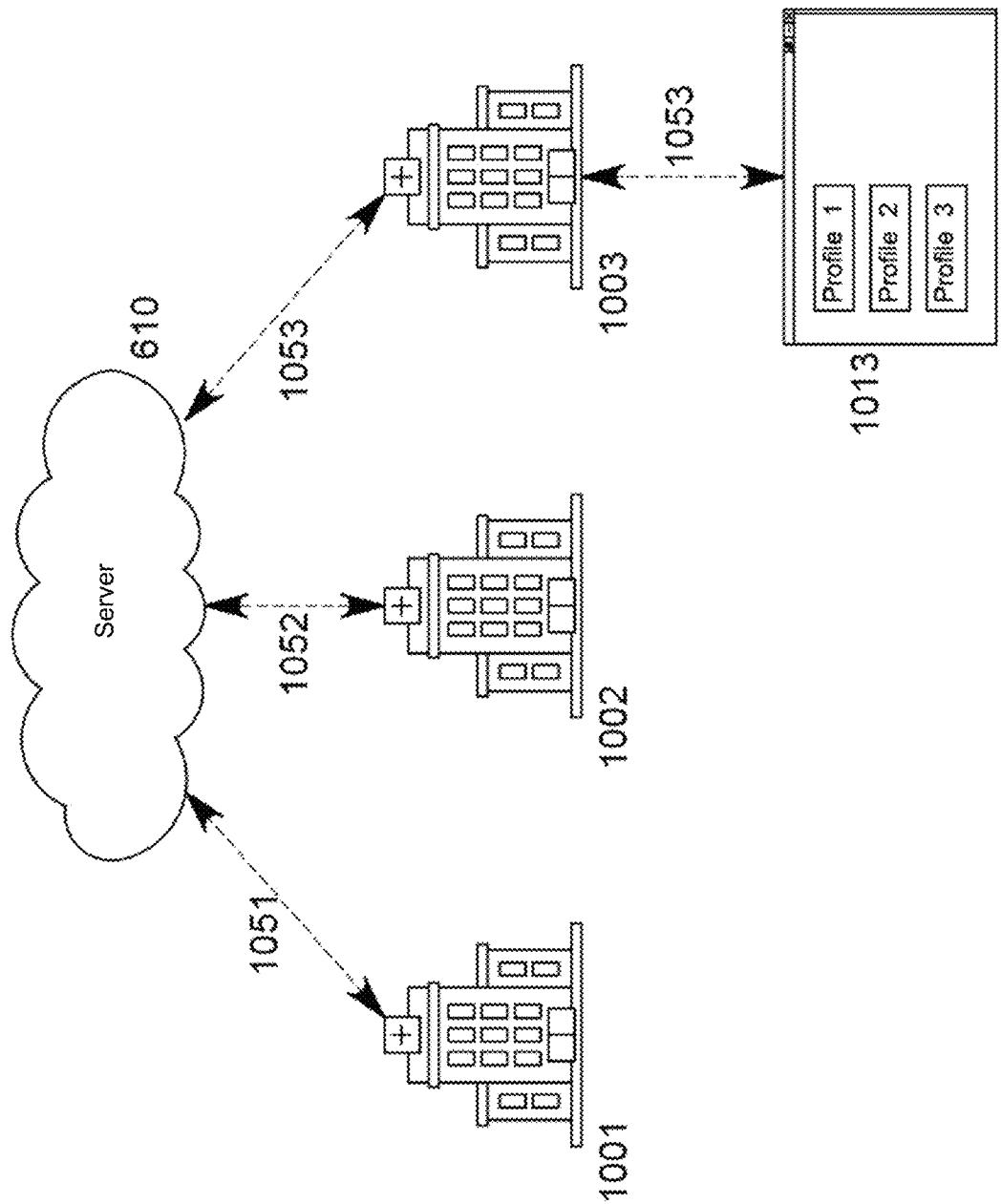
FIG. 10 depicts an example of a remote server communicating with multiple hospitals which have spaces that contain devices for continuous disinfection of human occupied space in accordance with some embodiments.

FIG. 10 depicts an example of a remote server communicating with multiple hospitals which have spaces that contain devices for continuous disinfection of human occupied space in accordance with some embodiments. In FIG.

10, remote server 610 communicates, via data transmission paths 1051, 1052, and 1053, with buildings 1001, 1002, and 1003, respectively. Typical examples of such buildings are hospitals, therapeutic centers, airports, etc.

Remote data transmission paths 1051, 1052, and 1053, with buildings 1001, 1002, and 1003, respectively, are performed by wireless technologies known in the art, for example, cellular and Internet.

Within buildings 1001, 1002, and 1003, data transmission paths 1051, 1052, and 1053, respectively, typically originate and are received by the computer 1013 of an administrator working within the building. Via the data transmission path with remote server 610, the administrator's computer screen 1013 can show the profiles of various spaces in the building that house the devices for continuous disinfection of human occupied space. Through this interface, the administrator can view the performance of and manage the operation of these devices.

Figure 11:
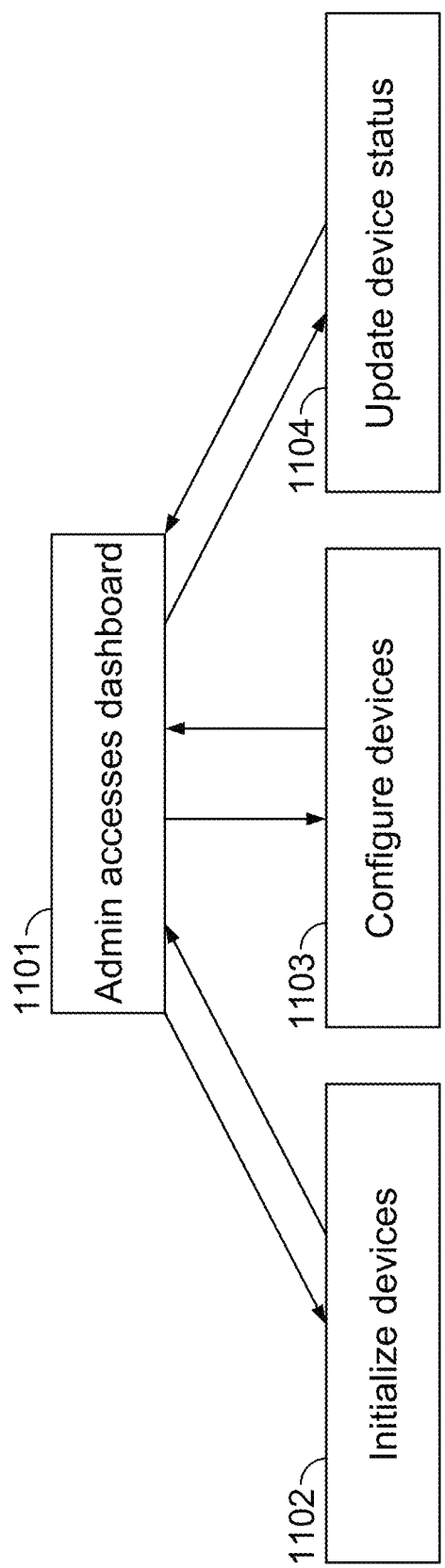
FIG. 11 is a flow diagram illustrating a process by which an administrator remotely controls devices in accordance with some embodiments.

FIG. 11 is a flow diagram illustrating process by which an administrator remotely controls a network of devices in accordance with some embodiments. For example, the administrator may be a hospital operation personnel, responsible for managing the network of devices being distributed around various rooms of the hospital. The administrator may access a UI dashboard through a personal computer, mobile phone, or other such device with a screen and UI controls.

Through this dashboard, the administrators can "on board" new devices 400, configure them, reset the default settings of one or more devices, edit their status, and so on. In some embodiments, each device 400 comes with default settings for its operations. But via the dashboard, the administrator can edit these defaults.

In Step 1101, the administrator views and operates a group of devices 400 via a UI dashboard presented on a computer, mobile phone, or other device with a screen and user control. The dashboard shows a view of the current status of all devices under control of the administrator. The group may include 2:n devices.

Through the dashboard, the administrator can review detailed data generated by the devices, for example, information on UV Levels received by people associated with each device or room (e.g., irradiance, dose, or other measurable UV level metric), total energy distributed throughout a room, current running status (e.g., run or standby), heat map, etc.

In some embodiments, the administrator can use the dashboard to view what one or more camera sensors 431 are picking up.

In Step 1102, the administrator initializes one or more new devices or existing devices that have been moved. Each device 400 must be physically mounted and aimed in a space or environment (e.g., a room, an elevator, a car, a train, a grocery store, a gym, a studio, a place of worship, a theater, or other any human occupied space). Once mounted, the next step for the administrator is to power on the devices.

In the case of multiple devices 400 in the same space, the next step is to pair the devices and set them up with a master/slave relationship. This step can be accomplished two different ways: (1) automatically; (2) via the administrator using the dashboard. In some embodiments, there is a single master device and a single slave device. In some embodiments, there is a single master device and a plurality of slave devices.

Regarding the automatic approach, any device in the space can serve as the master or the slave, it does not change the operation or functionality. In a default setting, the device that is first powered on is designated as the master, and any additional devices within that environment powered on later are the slaves. The devices detect each other via Wi-Fi or Bluetooth or wireless signals known in art prior to being paired via the admin.

In some embodiments, only devices with overlapping fields of illumination are paired. In some embodiments, a plurality of devices mounted within the same space are paired, regardless of whether their fields of illumination overlap. To ensure this, any devices that have the same space (e.g., same room) and are not paired are not permitted to run cycles. In some embodiments, each device displays a code on its surface, such a barcode or QR code, that enables other devices in the same space to identify that device with specificity, as well as employing the camera sensors to identify the other devices in the same space.

Regarding the administrator using the dashboard approach, the administrator pairs the new installed or moved devices via the dashboard. The admin either scans a code (e.g., barcode or QR code) or inputs the device serial number to connect with the specific device. This is done for each device. In one version of the setup the admin can then pair devices in a space assigning one to be the master and one to be the slave, using a mobile device app that displays the dashboard. The paired devices will then connect via Wi-Fi. Part of the setup concerns assigning a device to a particular space. Each device needs to appear on the dashboard with an associated space (e.g., room). With the new or moved devices installed and powered on, they will appear on the dashboard as devices needing to be initialized. Via the dashboard, through UI techniques known in the art, the administrator moves the new or moved devices into the proper UI "space" on the dashboard, and sets up the proper master/slave relationship for them.

Once pairing and master/slave relationship are complete (using either of the foregoing approaches), the devices in the space are then added to the dashboard and controlled via the admin by assigning them to a specific space displayed on the dashboard using UI techniques known in the art.

In Step 1103, the administrator configures one on more device 400 via the dashboard. Such configurations determine the specific rules of operation for the devices. One kind of such configuration is a "profile"—a set or group of rules related by a theme. Examples of such profiles include an ICU profile, default pathogen suppression profile, operating room profile, MRSA profile, Covid-19 profile, etc.

In addition to establishing profiles, the dashboard also enables the administrator to edit specific default settings (e.g., time for loop delays) for one or more devices. With one or more specific edits created by the administrator, the dashboard invites and enables the administrator to save these edits as a new profile.

In Step 1104, the current status of each device is updated on the dashboard. In some embodiments, this updating of status is accomplished by the dashboard periodically polling the devices for their current data. This data includes status (e.g., running cycle or on standby). Other data that is polled is total amount of UV light energy applied over various timer intervals, total amount of light energy patients have been exposed to over given time intervals, total amount of light energy different visitors, levels of exposure to doctors and healthcare workers. In some embodiments, the device for continuous disinfection of human occupied space is integrated with wearable technology, and individuals have total exposure profiles. In some embodiments, the device for continuous disinfection of human occupied space uses facial recognition technology, and individuals have access to total personal exposure profiles from that technology.

In some embodiments, updating the dashboard is accomplished by each device periodically gathering its current data and sending it to the dashboard. Examples of data that can be transmitted to the dashboard are hourly/daily summaries of UV light energy applied to the room; this can be correlated to log reductions in air or on surfaces. Events are classified, such as when mobile people enter and exit the room; this can be reported along with total UV exposure to those people within those events. In some embodiments, machine vision and machine learning technology for learning are utilized to recognize objects of interest such as IV poles and bed rails and calculate UV Level received by those surfaces. Data on objects and surfaces of interest are sent to the dashboard with UV exposure information and corresponding log reductions of various pathogens.

In addition to the current status of each device being updated on the dashboard periodically, this updating is also performed upon the occurrence of certain events, including Step 1102 (initialization) and Step 1103 (configuration).

FIG. 12 is a diagram illustrating a device with a sensor that can detect pathogens, and adjust the UV transmission accordingly in accordance with some embodiments. In the embodiment shown in FIG. 12, device 400 contains one or more of an additional sensor 1251 which serves to detect the presence of pathogens 1261, 1262. In other embodiments, sensor 1251 detects one or more of the count of said pathogens, their location, and their specific nature. Using any of the additional data in these other embodiments, device 400 is able to tailor a disinfection cycle for that specific pathogen.

In some embodiments, sensor 1251 is one or more of an air sampler, a sensor that can measure CO2 or other chemicals in the air that might correlate the room or space was recently occupied, a sensor that uses scattering for detection of pathogens, a nanomaterial based biosensor, a portable mass spectrometer that can be either co-located on device 400 or separate but still within the fields of illumination, and a sensor that uses spectroscopy.

Figure 13A:
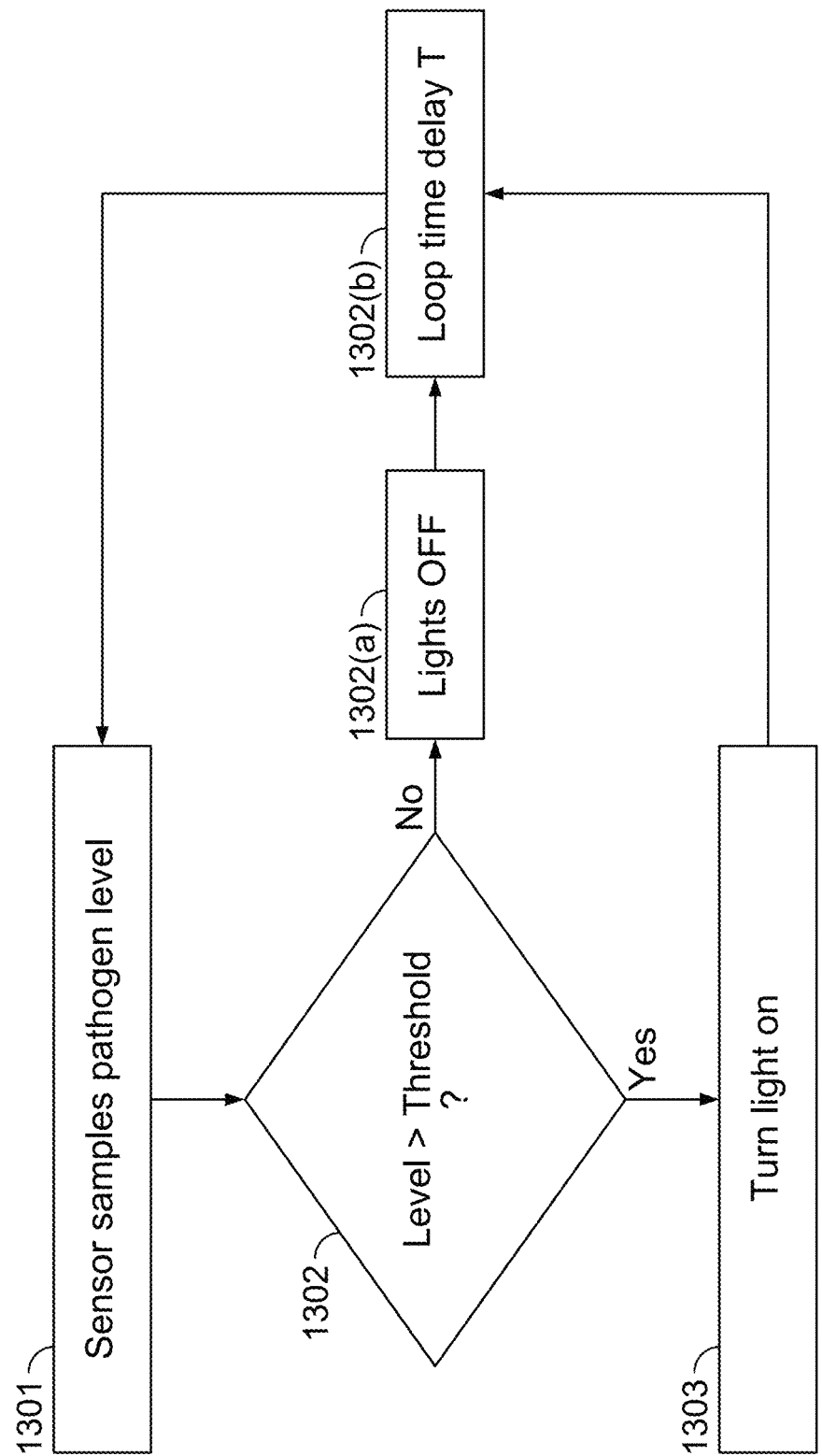
FIG. 13A is a flow diagram illustrating a process by which a device with a sensor that can detect pathogens adjusts the UV transmission accordingly in accordance with some embodiments.

FIG. 13A is a flow diagram illustrating a process by which a device with a sensor that can detect pathogens adjusts the UV transmission accordingly in accordance with some embodiments. FIG. 13A shows this process with the condition that no people are present in the room ("EMPTY SPACE"). FIG. 13A shows this process with the condition that people might or might not be present in the room ("OCCUPIED SPACE").

The functioning of the devices may transition from EMPTY SPACE state to OCCUPIED SPACE state for a room once the camera sensors detect a person present within the room. The transition from OCCUPIED SPACE to EMPTY SPACE occurs after a certain time period passes with no people detected in the room. In some embodiments, a default time period is established (for example, 30 minutes). Through the dashboard discussed earlier, the administrator can edit this time period per room, per building (set of rooms), or per multiple buildings being administered.

Operating in EMPTY SPACE state, the intensity of UV lamps may be set to a maximum value. This setting maximizes the rate of pathogen extermination. In some embodiments, the UV lamps are off during the EMPTY SPACE state to maintain life of the UV lamps. Operating in OCCUPIED SPACE state, the intensity of UV lamps may be set to a value less than the maximum value used for EMPTY STATE (for example, 75% of maximum). As with other settings, the administrator can edit this lower intensity for OCCUPIED SPACE. In OCCUPIED SPACE, the device can operate at 100% of maximum value if the defined limit of UV exposure (such as ACGIH TLVs) on occupants is maintained (depending on distance, angle, PPE, wavelength, eyes or skin exposure, etc.).

In step 1301 of FIG. 13A, the pathogen sensor in a device detects a level or concentration of pathogens present in the room.

In step 1302, controller 541 of the device checks whether the level detected in step 1301 exceeds a threshold. This threshold can be set according to the known art of pathogens and the concentration of them that provides a danger to the kind of people who occupy the room. This threshold can also be edited by the administrator via the dashboard.

In step 1302, if level>threshold, the process continues to step 1303 (i.e., the UV lights are turned on); otherwise, the process proceeds to step 1302(*a*) (i.e., the UV lights are turned off).

From each of steps 1303 and 1302(*a*), the process continues to step 1302(*b*), in which controller 541 of the device initiates a time delay T which must elapse before the process returns to step 1301. As with other system default, the value of T can be edited by the administrator via the dashboard.

Figure 13B:
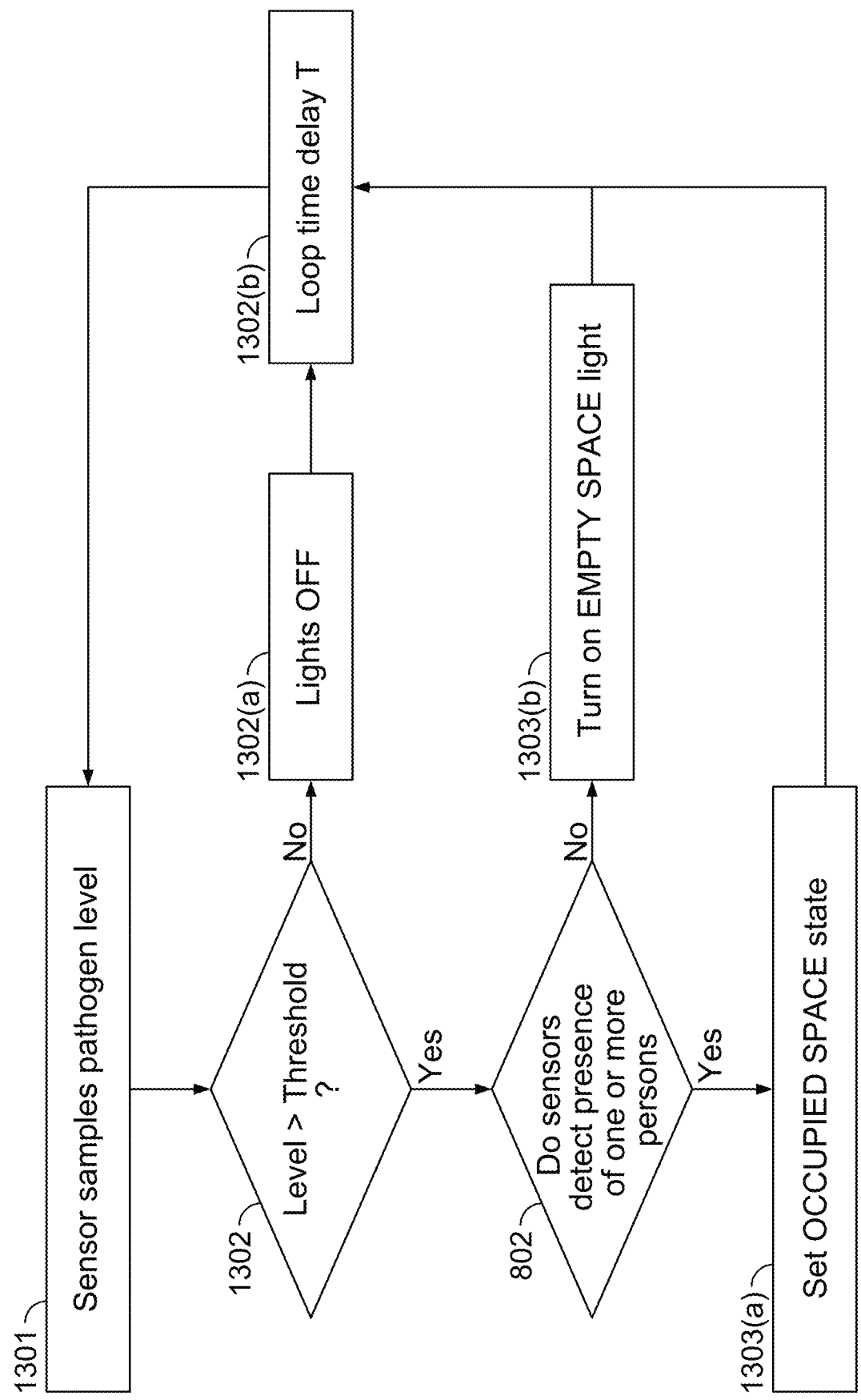
FIG. 13B is a flow diagram illustrating a process by which a device with a sensor that can detect pathogens adjusts the UV transmission accordingly in accordance with some embodiments.

For FIG. 13B, steps 1301, 1302, 1302(*a*), and 1302(*b*) are the same as for FIG. 13A. FIG. 13A differs from FIG. 13B in the case that step 1302 (level>threshold) is true. With this condition, the process continues to step 802.

As with FIG. 8, in step 802, one or more of camera sensors 431 and 432 checks whether it can detect the presence of one or more persons. If a person is detected in step 802, the process continues to step 1303(*a*); otherwise, to 1303(*b*).

In step 1303(*a*), the operating condition is set to OCCUPIED SPACE state. In this state, the discussion for FIGS. 8 and 9 describe how the UV lights are turned on and off depending upon the presence of people and/or the distance and angles to those people.

In step 1303(*b*), the operating condition is set to EMPTY SPACE state and turns on the UV lamps to maximum intensity.

From both steps 1303(*a*) and 1303(*b*), the process continues to step 1302(*b*) (discussed for FIG. 13A).

Figure 14:
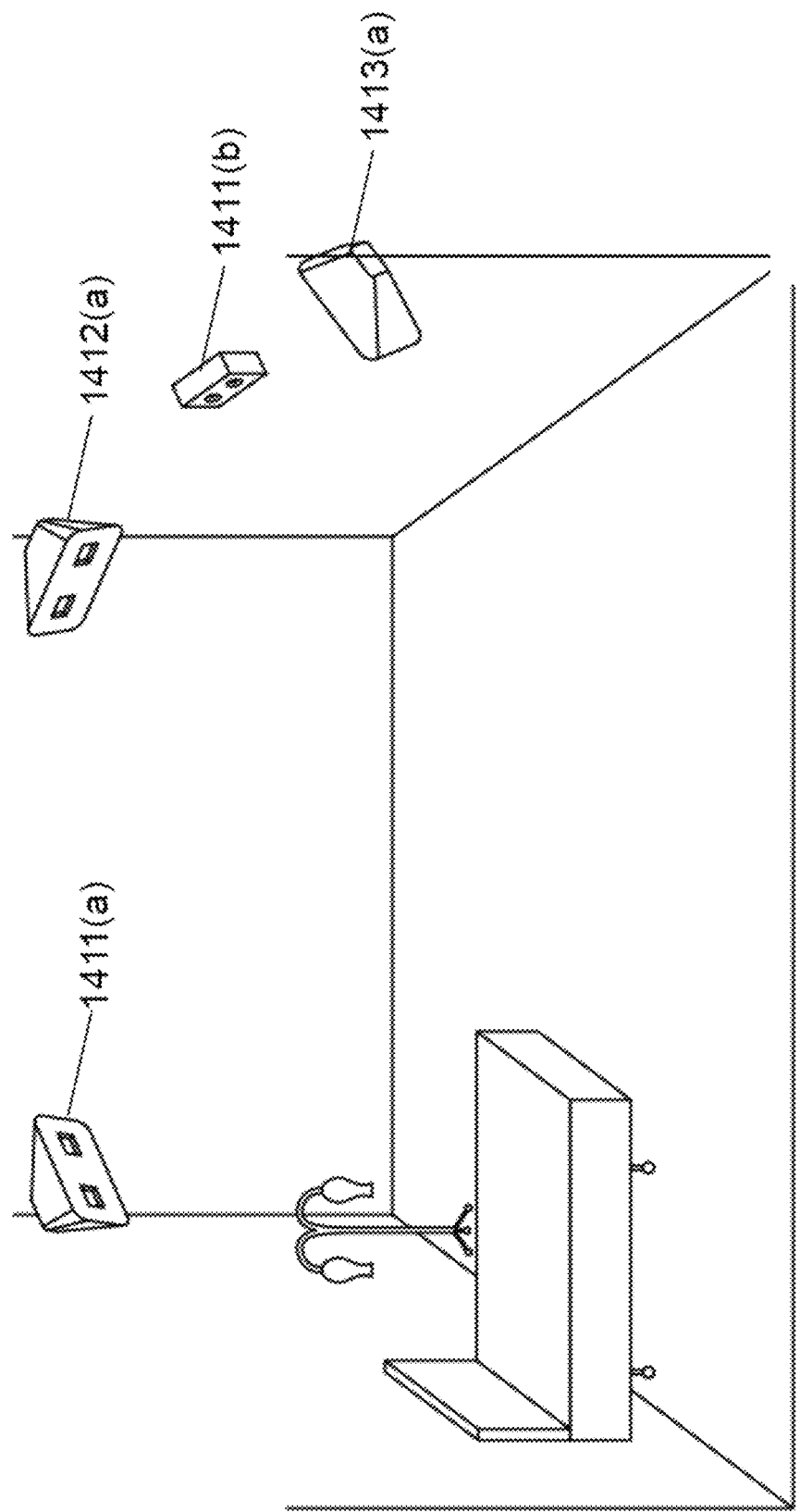
FIG. 14 is a diagram illustrating a system that includes UV lamps and camera sensors deployed as physically independent devices in accordance with some embodiments.

The embodiment of FIG. 4 is one of many embodiments of the device for continuous disinfection of human occupied space. Other models of UV lamps and camera sensors can be used. Also, in some embodiments, physically independent devices are used for the UV lamps versus the camera sensors. In some cases, it is advantageous to locate the sensors that detect the presence of people separately from the UV light source. When separated from the source, the sensors and associated computing means process the algorithms described in FIGS. 8 and 9, for example, transmitting the on-off light commands to the light source. FIG. 14 shows an embodiment of the device for continuous disinfection of human occupied space with the UV lamps 1411(*a*), 1412(*a*), and 1413(*a*) and camera sensors 1411(*b*) deployed as physically independent devices.

In some embodiments, a device with one or more UV lamps includes one or more stereoscopic cameras capable of sensing the entire room. As with FIG. 14, such stereoscopic cameras can be integrated into devices separated from the UV lamp devices.

Figure 15:
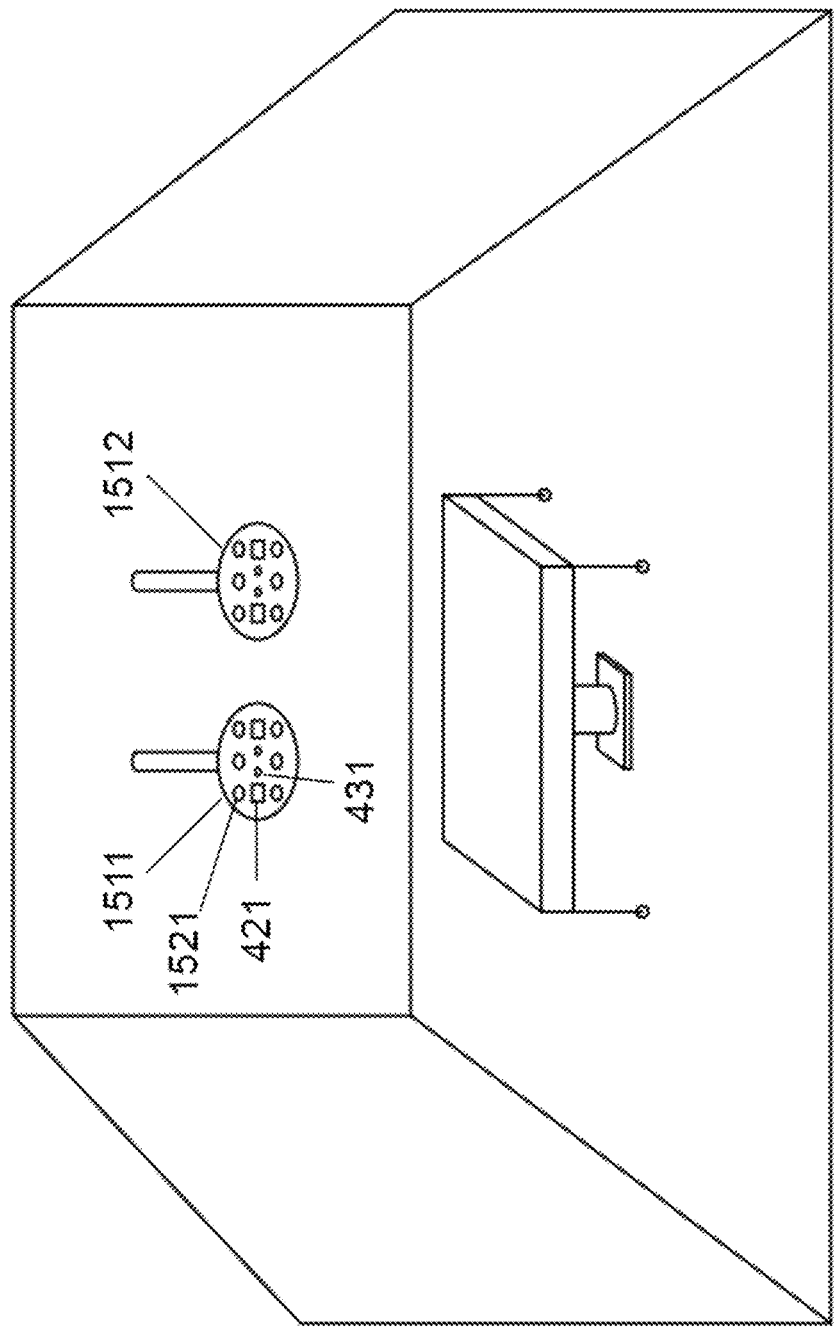
FIG. 15 shows a diagram of a system that includes a device for continuous disinfection of human occupied space being integrated into overhead surgical lights in accordance with some embodiments.

In some embodiments, device 400 assumes the form and function of existing fixtures and other items commonly present in the room, such as common room light fixtures and hospital operating room devices (e.g., spot lights). No matter the form of device 400 (e.g. FIG. 4 or an IV drip), the same functions described herein are performed. FIG. 15 is a diagram illustrating a system that includes a device for continuous disinfection of human occupied space being integrated into overhead surgical lights 1511 and 1512 in accordance with some embodiments. For example, focusing on surgical light 1511, shown on FIG. 15 are UV lamp 421 (one of two), camera sensor 431 (one of two), and surgical lamp 1511 (one of four).

Figure 16A:
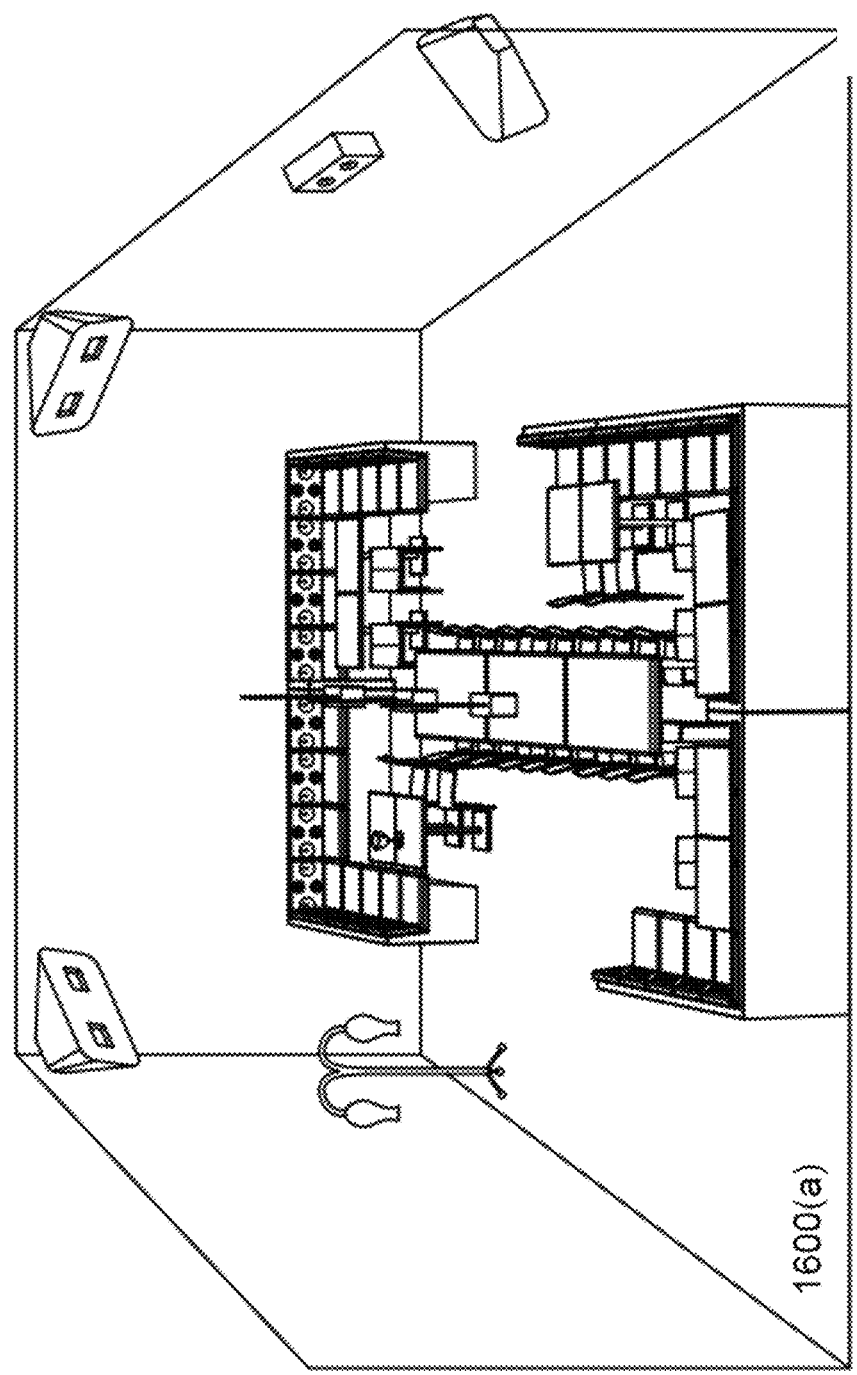
FIG. 16A is a diagram illustrating a system that includes a device for continuous disinfection of human occupied space being deployed in a restaurant environment in accordance with some embodiments.
Figure 16B:
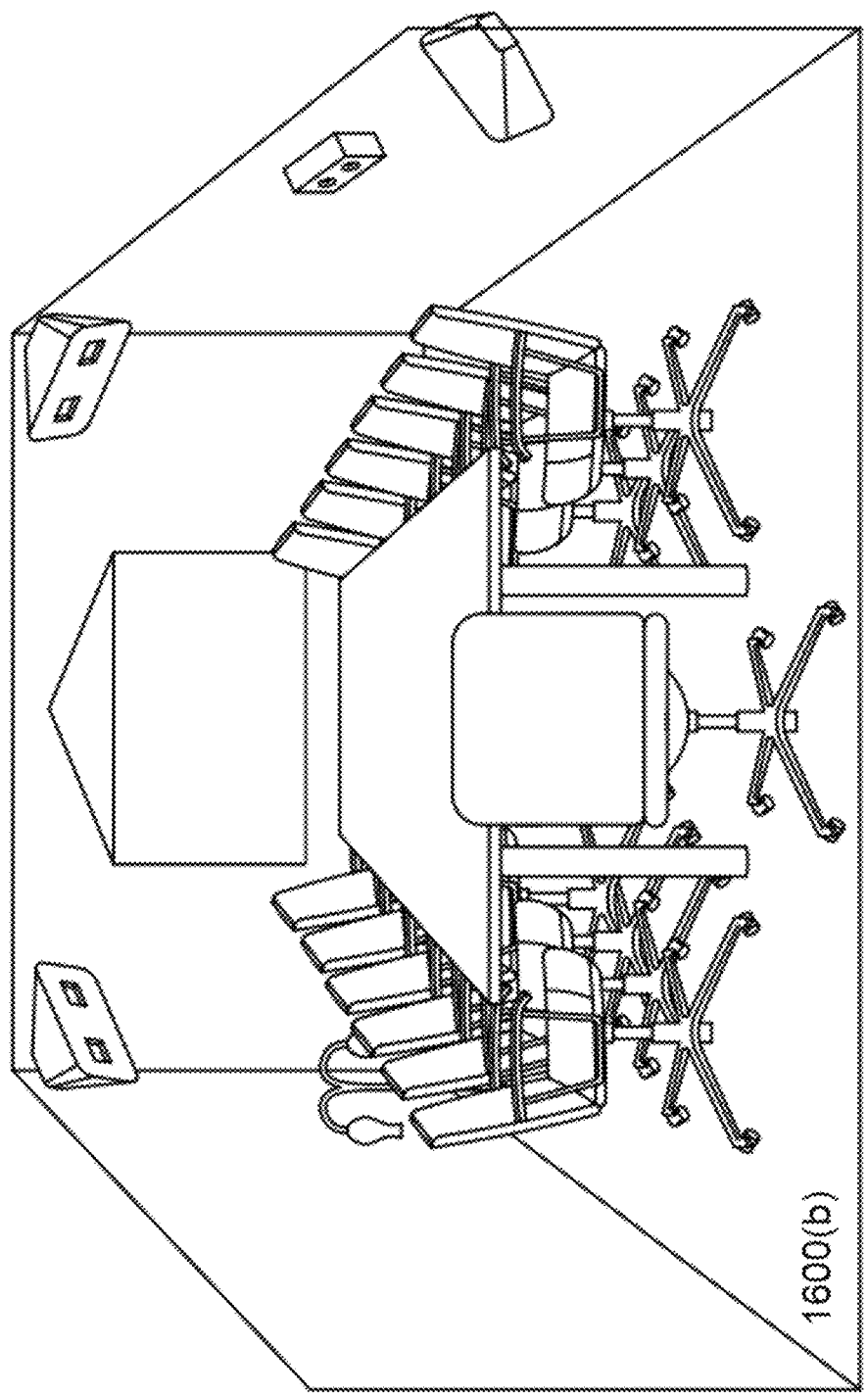
FIG. 16B is a diagram illustrating a system that includes a device for continuous disinfection of human occupied space being deployed in a conference room environment in accordance with some embodiments.
Figure 16C:
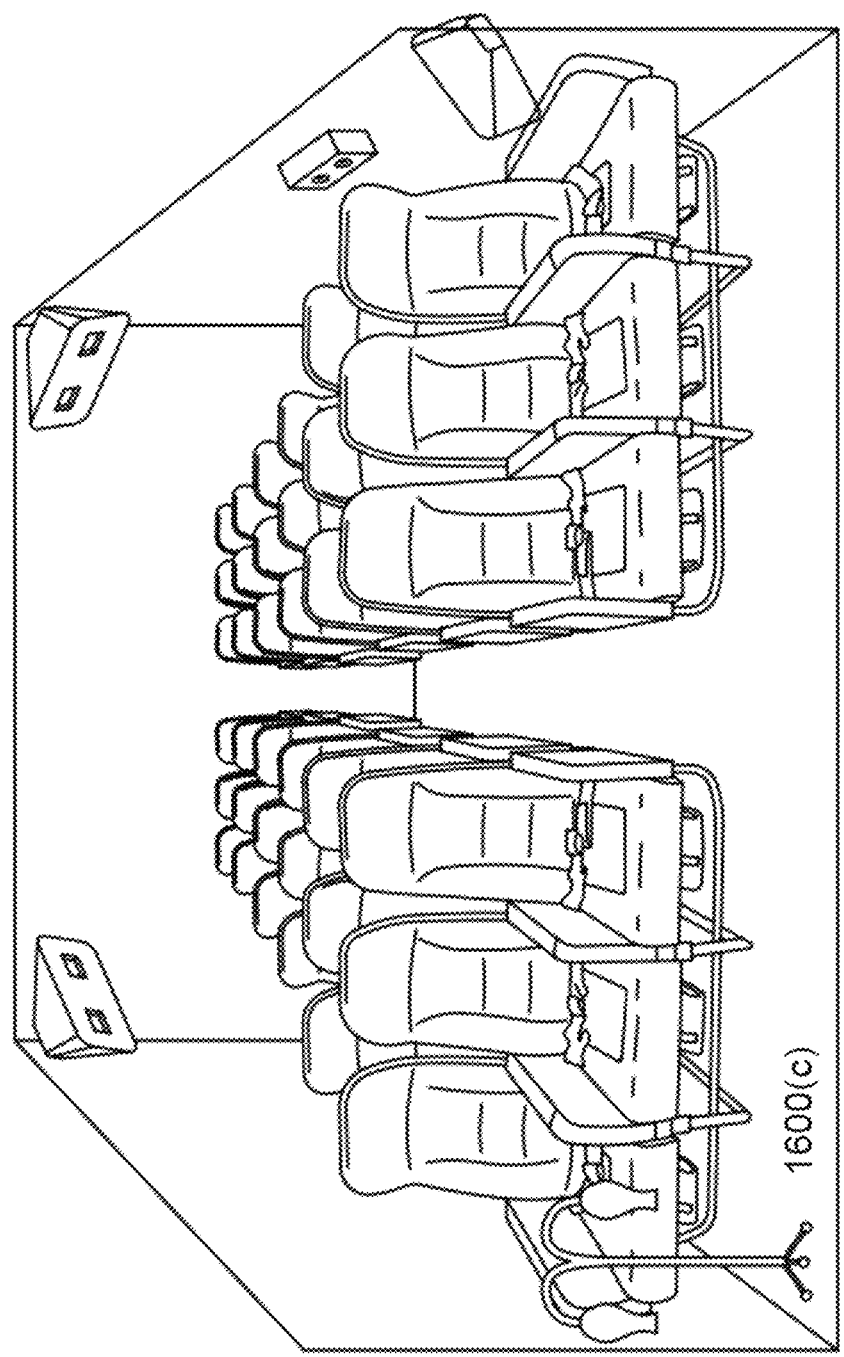
FIG. 16C is a diagram illustrating a system that includes a device for continuous disinfection of human occupied space being deployed in an airplane environment in accordance with some embodiments.

FIG. 16A-16C shows the device for continuous disinfection of human occupied space deployed in various environments. Examples of these environments include a restaurant 1600(*a*) (FIG. 16A), an office conference room 1600(*b*) (FIG. 16B), and an airplane cabin 1600(*c*) (FIG. 16C). These environments are a few among the unlimited types of rooms and spaces in which the device for continuous disinfection of human occupied space can be deployed. Other environments may include an elevator, a car, a train, a grocery store, a gym, a studio, a place of worship, a theater, or other any human occupied space.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system, comprising:
one or more ultraviolet (UV) light sources;
one or more sensors configured to detect a presence of one or more people in a space; and
a processor coupled to the one or more UV light sources and the one or more sensors, wherein the processor is configured to calculate a UV light level delivered in the space while the space is occupied with the one or more people based on a first output of the one or more UV light sources and a second output of the one or more sensors, wherein to calculate the UV light level delivered in the space while the space is occupied with the one or more people, the processor is configured to:
determine an instantaneous UV light level for each of the one or more people in the space;
determine a maximum instantaneous UV light level among the determined instantaneous UV light level for each of the one or more people in the space; and
compare the determined maximum instantaneous UV light level to a limit.

2. The system of claim 1, wherein the one or more sensors are configured to detect a corresponding location of the one or more people in the space.

3. The system of claim 2, wherein the corresponding location of the one or more people in the space is associated with a corresponding upper body of the one or more people.

4. The system of claim 2, wherein the corresponding location of the one or more people in the space is associated with a corresponding head of the one or more people.

5. The system of claim 1, wherein the UV light level is an irradiance delivered in the space while the space is occupied.

6. The system of claim 1, wherein the UV light level is a dose of UV light delivered in the space for a particular period of time.

7. The system of claim 1, wherein the processor is configured to control at least one of the one or more UV light sources in response to a determination that the determined maximum instantaneous UV light level is greater than the limit.

8. The system of claim 7, wherein the at least one of the one or more UV light sources is turned off for a particular amount of time.

9. The system of claim 1, wherein the processor is configured to maintain the one or more UV light sources in an on state in response to a determination that the determined maximum instantaneous UV light level is not greater than the limit.

10. The system of claim 1, wherein in response to detecting of the one or more people in the space, the processor is configured to modulate the UV light level associated with at least one of the one or more UV light sources from a first UV light level to a second UV light level.

11. The system of claim 10, wherein the first UV light level causes an irradiance of 40 uW/cm$^2$ to be received within a field of illumination associated with the at least one of the one or more UV light sources.

12. The system of claim 10, wherein the second UV light level causes an irradiance of 16.35 uW/cm$^2$ or less to be received within a field of illumination associated with the at least one of the one or more UV light sources.

13. The system of claim 10, wherein the second UV light level causes an irradiance of 5.59 uW/cm$^2$ or less to be received within a field of illumination associated with the at least one of the one or more UV light sources.

14. The system of claim 1, wherein the one or more sensors include a camera, radar, lidar, time-of-flight, a motion sensor, a thermal sensor, an infrared sensor, a carbon dioxide sensor, and/or a combination thereof.

15. The system of claim 1, wherein the one or more UV light sources include a first UV device, the system further comprising a second UV device, wherein the first UV device and the second UV device are configured to communicate UV level data to each other.

* * * * *